United States Patent
Vadlamudi et al.

(10) Patent No.: US 10,682,388 B2
(45) Date of Patent: Jun. 16, 2020

(54) TARGETING OF PELP1 IN CANCER THERAPY

(71) Applicant: THE BOARD OF REGENTS OF THE UNIVERSITY OF TEXAS SYSTEM, Austin, TX (US)

(72) Inventors: Ratna K. Vadlamudi, San Antonio, TX (US); Monica Mann, Austin, TX (US); Samaya Krishnan, San Antonio, TX (US); Gangadhara Reddy Sareddy, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/110,426

(22) PCT Filed: Jan. 14, 2015

(86) PCT No.: PCT/US2015/011377
§ 371 (c)(1),
(2) Date: Jul. 8, 2016

(87) PCT Pub. No.: WO2015/108955
PCT Pub. Date: Jul. 23, 2015

(65) Prior Publication Data
US 2017/0165320 A1    Jun. 15, 2017

Related U.S. Application Data

(60) Provisional application No. 61/927,743, filed on Jan. 15, 2014.

(51) Int. Cl.
| | |
|---|---|
| *C07K 7/06* | (2006.01) |
| *C07K 7/08* | (2006.01) |
| *C07K 14/00* | (2006.01) |
| *A61K 38/16* | (2006.01) |
| *A61K 38/10* | (2006.01) |
| *A61K 38/04* | (2006.01) |
| *A61K 45/06* | (2006.01) |

(52) U.S. Cl.
CPC .............. *A61K 38/16* (2013.01); *A61K 38/04* (2013.01); *A61K 38/10* (2013.01); *A61K 45/06* (2013.01); *C07K 7/06* (2013.01); *C07K 7/08* (2013.01); *C07K 14/00* (2013.01)

(58) Field of Classification Search
None
See application file for complete search history.

(56) References Cited

U.S. PATENT DOCUMENTS

| | | | |
|---|---|---|---|
| 7,256,256 B1 * | 8/2007 | Paterson | A61K 38/10 435/69.1 |
| 2008/0234183 A1 * | 9/2008 | Hallbrink | A61K 51/0448 514/1.1 |
| 2013/0330335 A1 * | 12/2013 | Bremel | G06F 19/18 424/134.1 |

FOREIGN PATENT DOCUMENTS

WO    WO 2012/123119 A1    9/2012

OTHER PUBLICATIONS

Nair et al., PELP1 is a reader of histone H3 methylation that facilitates oestrogen receptor-alpha target gene activation by regulating lysine demethylase 1 specificity, EMBO reports, 2010, pp. 438-444.*

Mann et al., "Inhibition of PELP1 Oncogenic Functions with Cell-Penetrating Peptides", Abstract OR24-2, The Endocrine Society's 94th Annual Meeting and Expo, Jun. 2012; cited in the IDS filed May 26, 2017.*

Bird et al., "Chemical Synthesis of Hydrocarbon-Stapled Peptides for Protein Interaction Research and Therapeutic Targeting", Curr Protoc Chem Biol. 2011; pp. 99-117 (document pp. 1-22) (Year: 2011).*

Synder et al., "Cell Penetrating Peptides in Delivery", Pharmaceutical Research, 2004, pp. 389-393 (Year: 2004).*

Bird et al., ChemicalSynthesis of Hydrocarbon-Stapled Peptides for Protein Interaction Research and Therapeutic Targeting, Curr Protoc Chem Biol., 2011, 99-117 (Year: 2011).*

Mann, et al., "PELP1 oncogenic functions involve CARM1 regulation." *Carcinogenesis* Jul. 2013, 34(7):1468-75; Abstract , p. 1471, col. 2.

Mann, et al. Abstract P1-05-10: "Targeting breast cancer metastasis through disruption of novel PELP1-G9a complex." *Cancer Res* 2012, 72(24 Suppl):Abstract No. P1-05-10; [Retrieved from the Internet Apr. 2, 2015: http://cancerres.aacrjournals.org/contenV72/24_SupplemenVP1-05-10.short]; in entirety.

Mann, et al. OR24-2: Inhibition of PELP1 Oncogenic Functions With Cell-Penetrating Peptides. The Endocrine Society's 94th Annual Meeting and Expo, Jun. 23-26, 2012—Houston, TX [Retrieved from the Internet Apr. 2, 2015: <http://press.endocrine.org/doi/abs/10.1210/endomeetings.2012.NRSH.2.0R24-2>]; in entirety.

PCT International Search Report and Written Opinion issued in International Application PCT/US15/1377 dated Jun. 4, 2015.

PCT International Preliminary Report on Patentability issued in International Application PCT/US15/11377 dated Jul. 19, 2016.

Mann M and Vadlamudi RK. Modulation of breast cancer epigenetics through the novel PELP1-G9a complex. Keystone Symposium: Epigenetic Marks and Cancer Drugs, 2013, Santa Fe, NM.

(Continued)

*Primary Examiner* — Lianko G Garyu
(74) *Attorney, Agent, or Firm* — Parker Highlander PLLC

(57) ABSTRACT

The disclosure describes PELP1 binding peptides and peptoids and their use the interaction of PELP1 with molecules that lead to oncogenic signaling in cancers.

15 Claims, 16 Drawing Sheets
(16 of 16 Drawing Sheet(s) Filed in Color)
Specification includes a Sequence Listing.

(56) References Cited

OTHER PUBLICATIONS

Mann M and Vadlamudi RK. Target breast cancer metastasis through PELP1-G9a complex. San Antonio Breast Cancer Symposium CTRC-AACR, 2012, San Antonio, TX.

Mann M and Vadlamudi RK. Inhibition of PELP1 oncogenic functions with cell permeable peptides. Cancer Prevention and Research Institute Conference, 2012, Austin, TX.

Mann M and Vadlamudi RK. Inhibition of PELP1 oncogenic functions with cell penetrating peptides. The Endocrine Society, 2012, Houston, TX.

Mann M, Zurcher G and Vadlamudi RK. Novel cell permeable inhibitors of PELP1 oncogenic functions. American Association for Cancer Research, 2012, Chicago, IL.

Azorsa et al., "Association of steroid receptor coactivator AIB1 with estrogen receptor-alpha in breast cancer cells." *Breast Cancer Research and Treatment*, Nov. 2001, 70:89-101.

Cortez et al., "Targeting the PELP1-KDM1 axis as a potential therapeutic strategy for breast cancer." *Breast Cancer Research*, Jul. 2012, 14:R108.

Epsztejn-Litman et al., De novo DNA methylation promoted by G9a prevents reprogramming of embryonically silenced genes. *Nature Structural & Molecular Biology*, Nov. 2008, 15:1176-1183.

Fillmore et al., "Estrogen expands breast cancer stem-like cells through paracrine FGF/Tbx3 signaling." *Proceedings National Academy Sciences USA*, Dec. 2010, 107:21737-21742.

Grigoryev, Y., "Stapled peptide to enter human testing, but affinity questions remain." *Nature Medicine*, Feb. 2013, 19:120.

Habashy et al., "The prognostic significance of PELP1 expression in invasive breast cancer with emphasis on the ER-positive luminal-like subtype." *Breast Cancer Research and Treatment*, Apr. 2010, 120:603-612.

Kumar et al., "Extranuclear coactivator signaling confers insensitivity to tamoxifen." *Clinical Cancer Research* Jun. 2009, 15:4123-4130.

List et al., "Expression of the nuclear coactivator AIB1 in normal and malignant breast tissue." *Breast Ccancer Research and Treatment*, Jul. 2001, 68:21-28.

Mann et al., "PELP1 oncogenic functions involve CARM1 regulation." *Carcinogenesis*, Jul. 2013, 34(7):1468-75.

Nair et al., "Roscovitine confers tumor suppressive effect on therapy-resistant breast tumor cells." *Breast Cancer Research*, Aug. 2011, 13:R80.

Phillips et al., "Design and structure of stapled peptides binding to estrogen receptors." *Journal American Chemical Society*, Jun. 2011, 133:9696-9699.

Purcell et al., "A distinct mechanism for coactivator versus corepressor function by histone methyltransferase G9a in transcriptional regulation." *Journal Biological Chemistry*, Dec. 2011, 286:41963-41971.

Tachibana et al., "G9a histone methyltransferase plays a dominant role in euchromatic histone H3 lysine 9 methylation and is essential for early embryogenesis." *Genes & Development*, Jul. 2002, 16:1779-1791.

Torres-Arzayus et al., "High tumor incidence and activation of the PI3K/AKT pathway in transgenic mice define AIB1 as an oncogene." *Cancer Cell*, Sep. 2004, 6:263-274.

Vallabhaneni et al., "Significance of ER-Src axis in hormonal therapy resistance." *Breast Cancer Research and Treatment*, Nov. 2011, 130:377-385.

Walensky et al., "Activation of apoptosis in vivo by a hydrocarbon-stapled BH3 helix." *Science*, Sep. 2004, 305:1466-1470.

\* cited by examiner

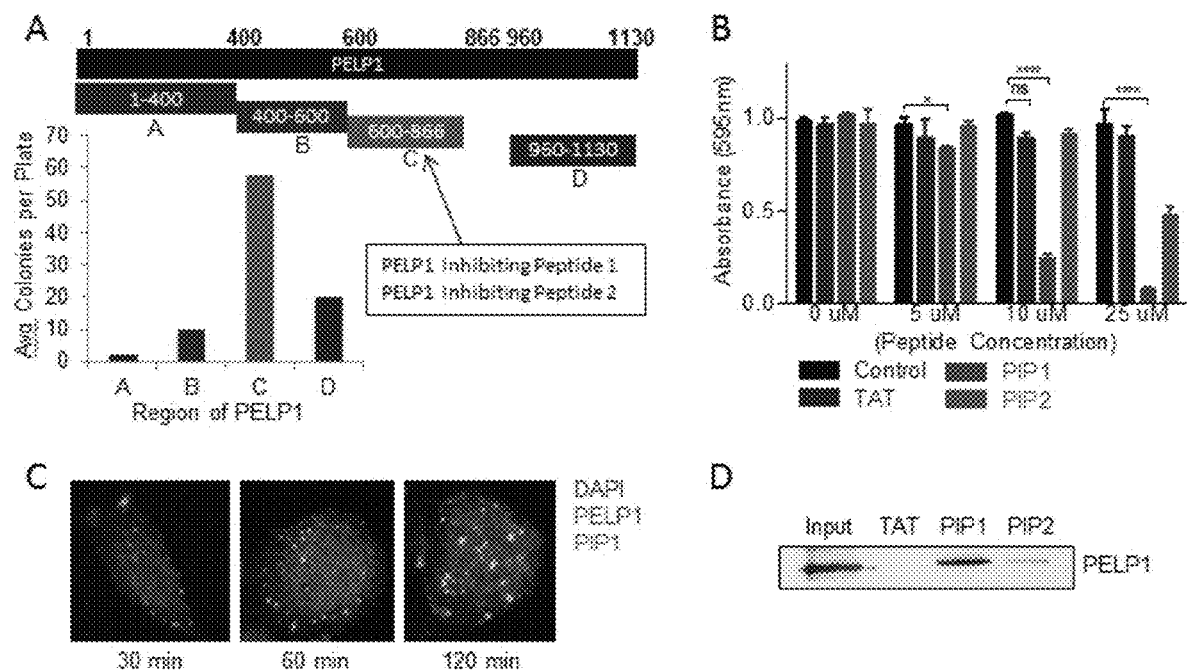
FIGS. 1A-D
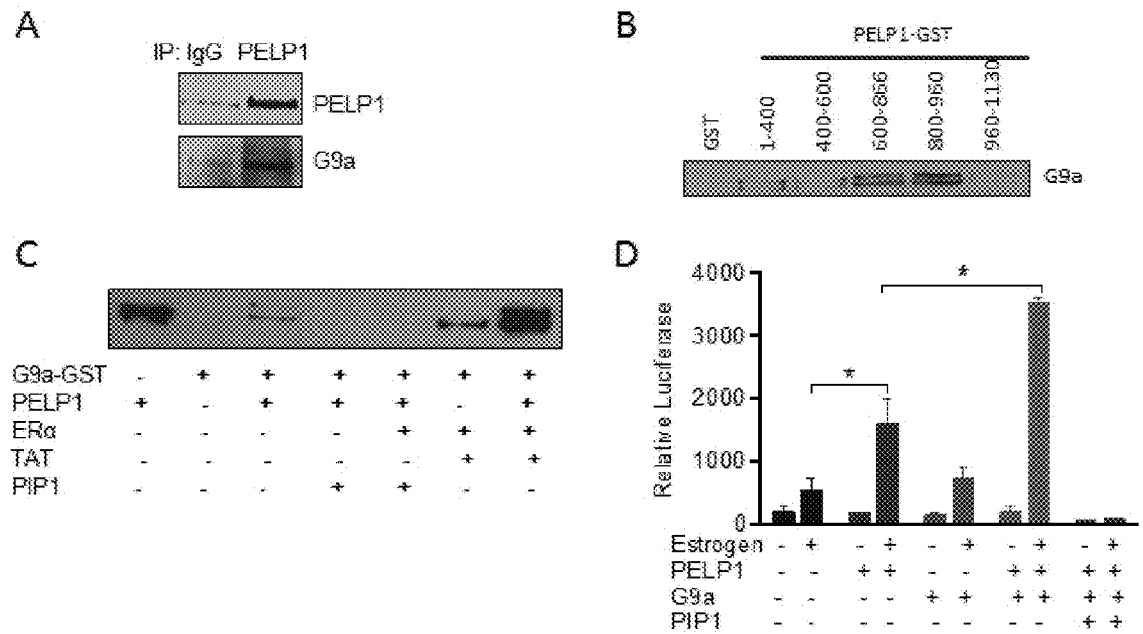
FIGS. 2A-D

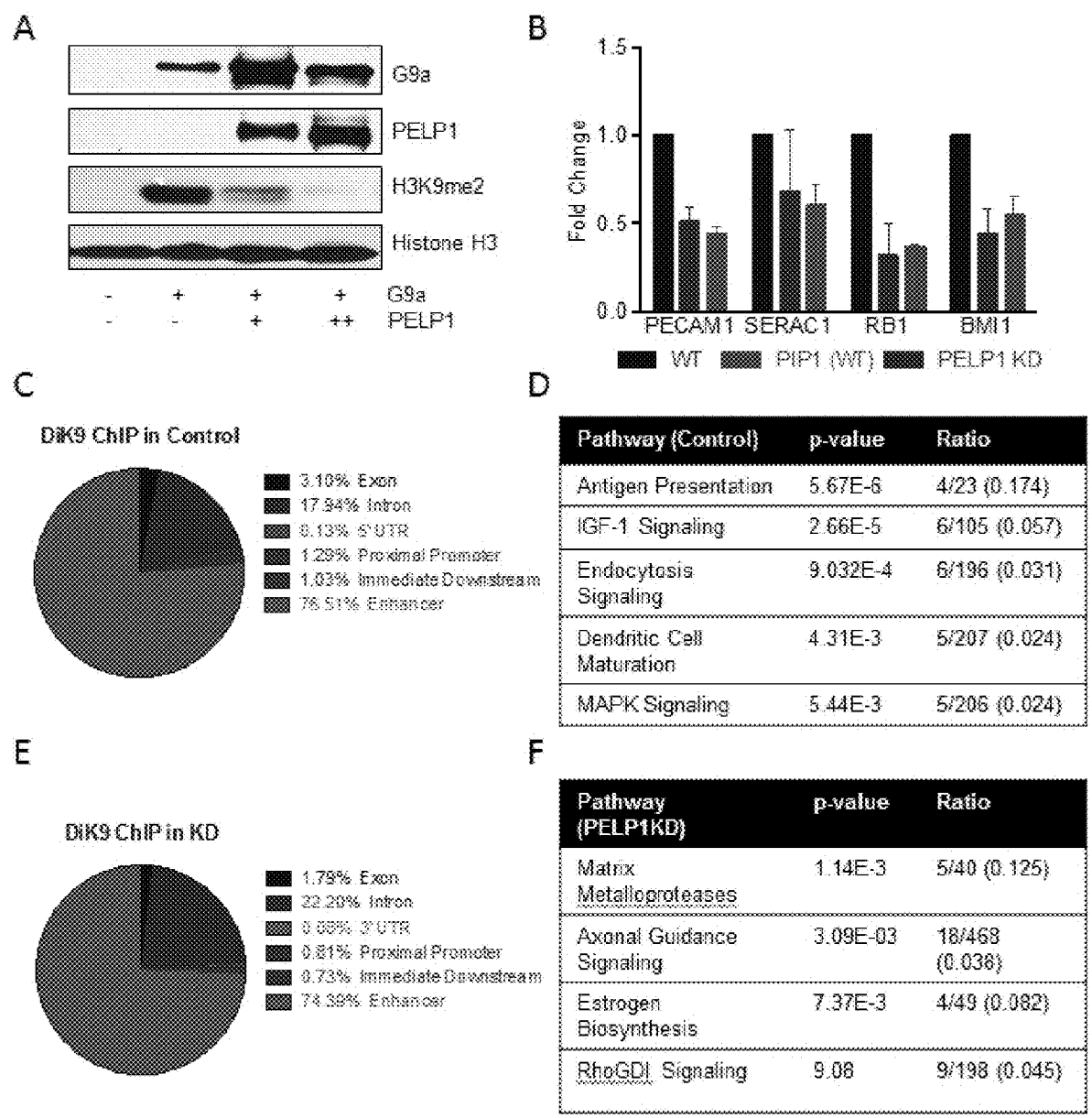
FIGS. 3A-F

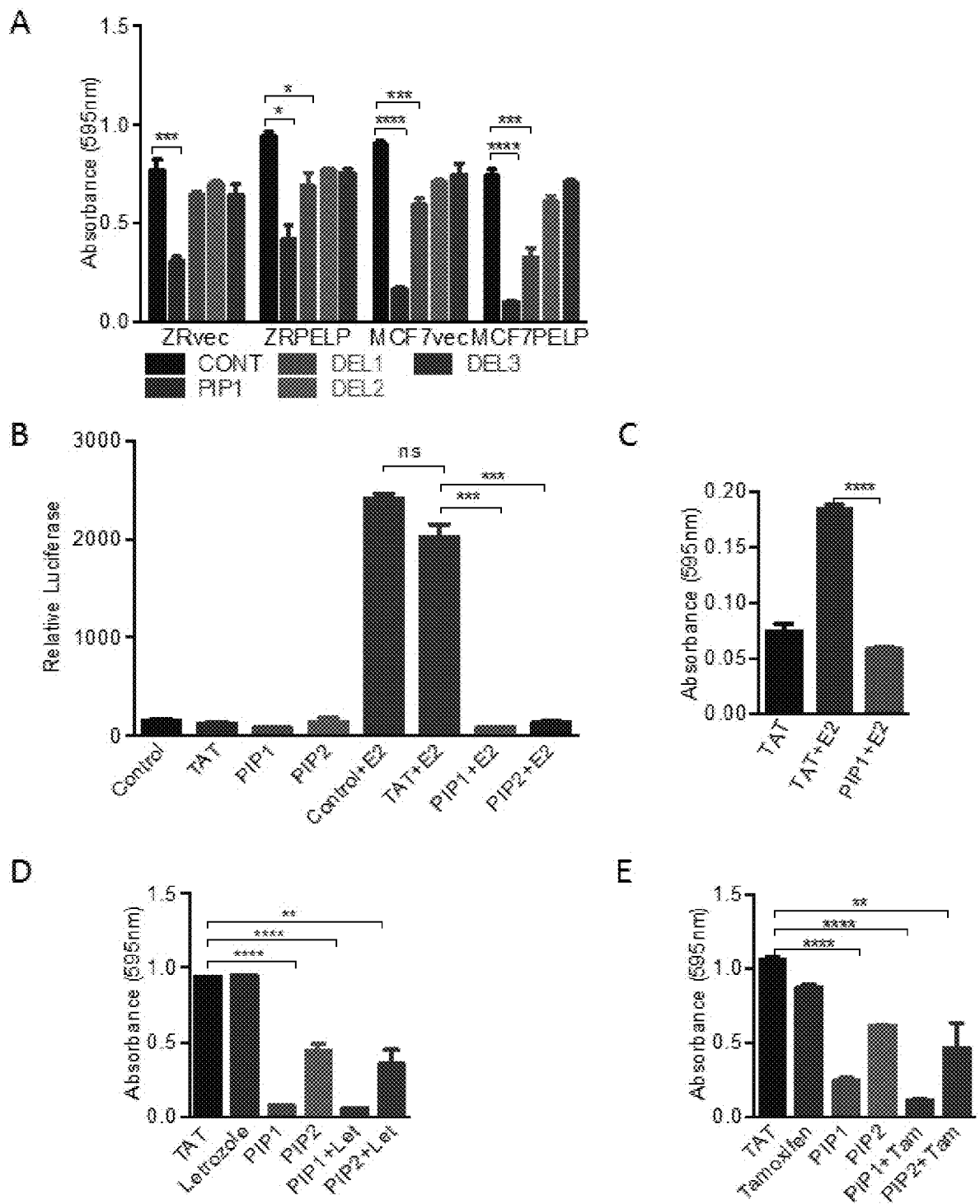
FIGS. 4A-E

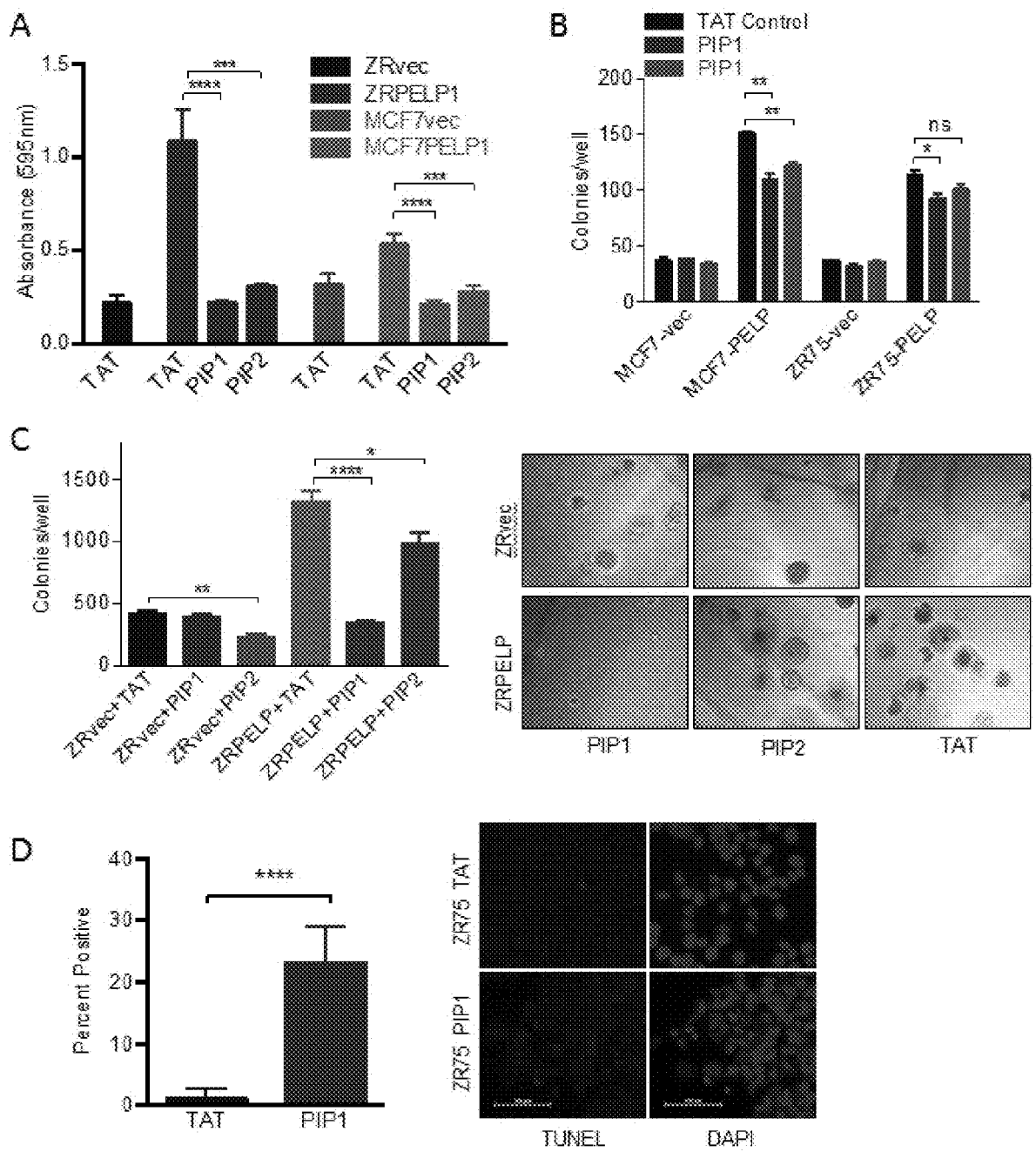
FIGS. 5A-D

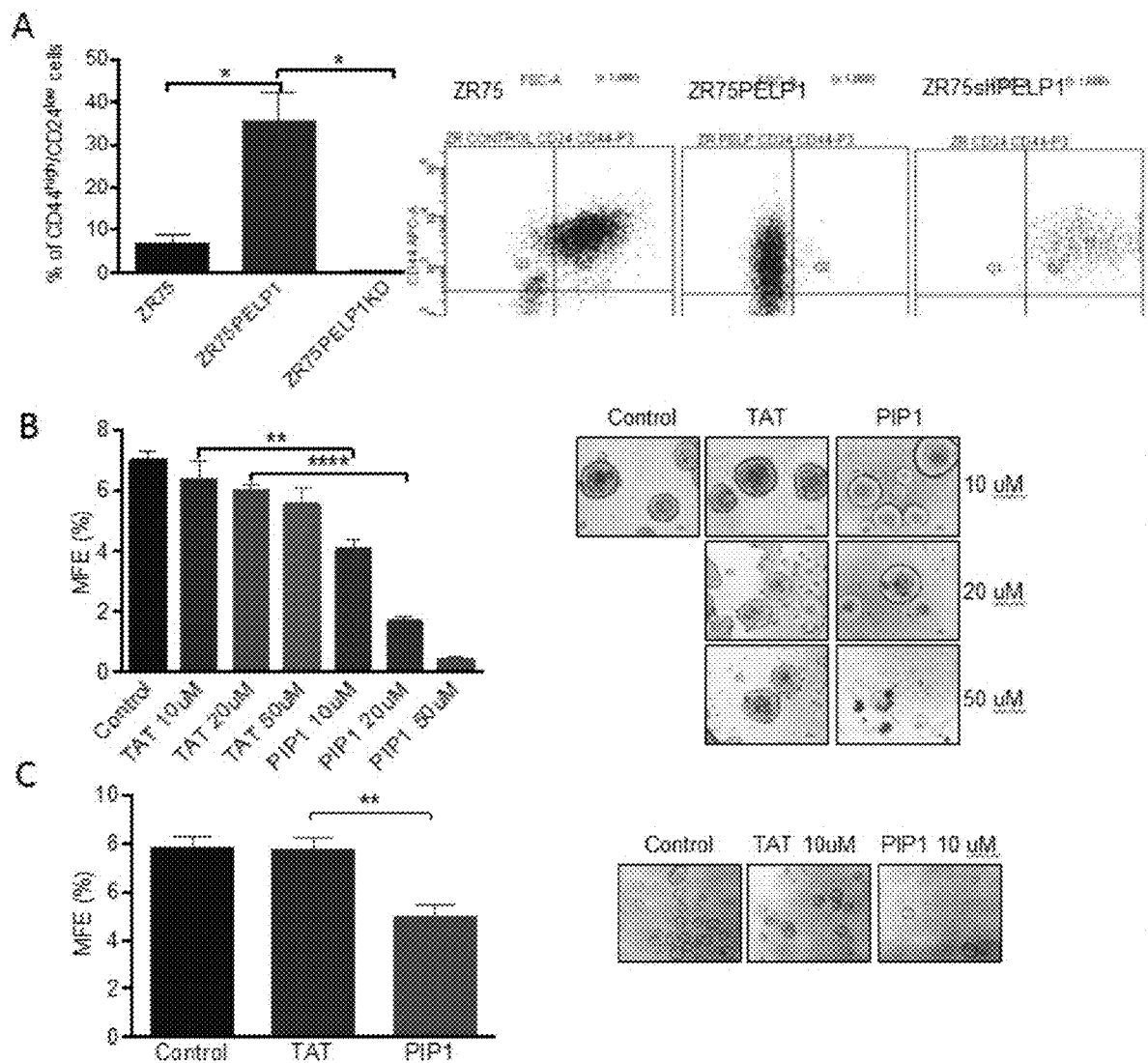
FIGS. 6A-C

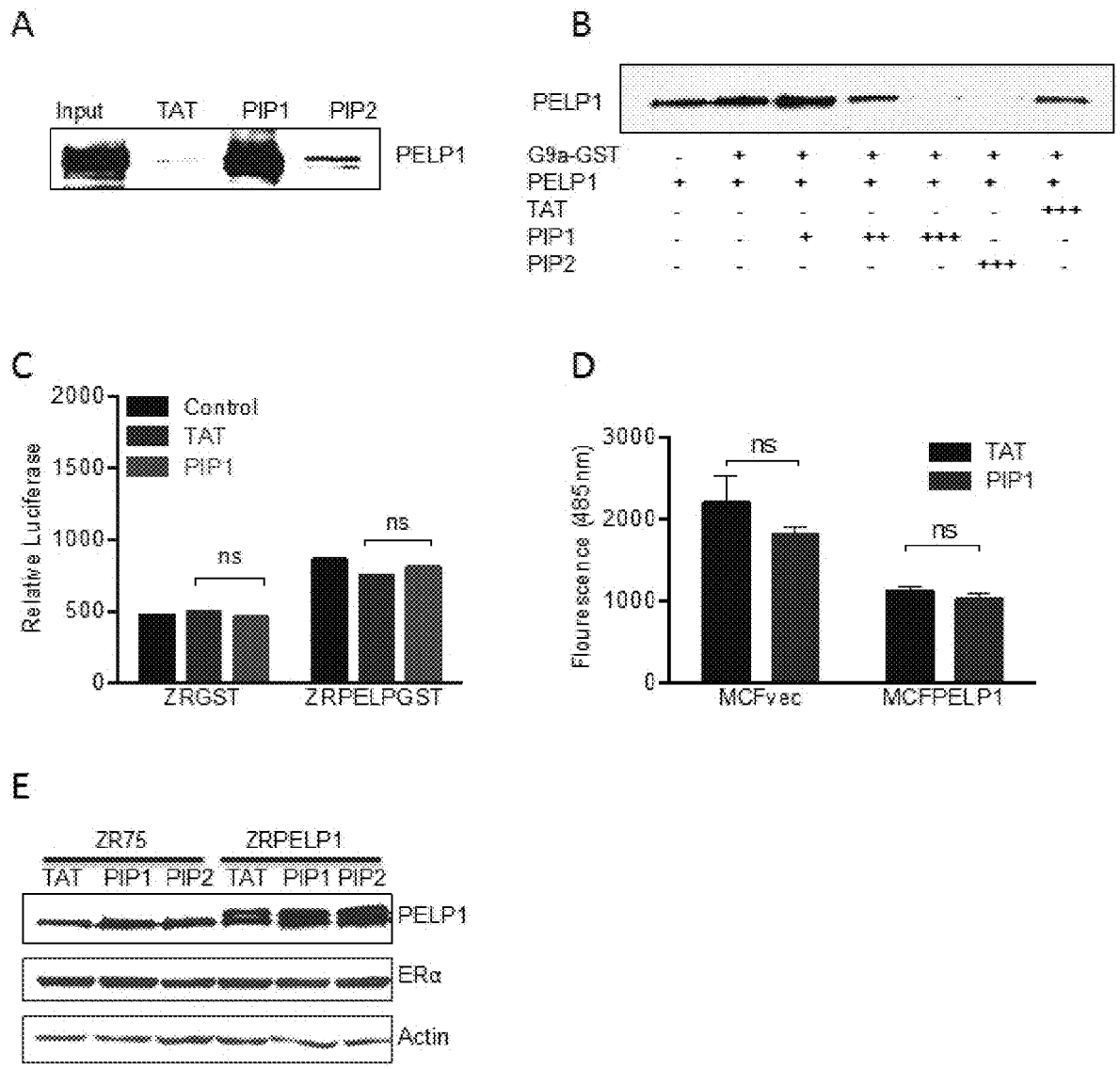
FIGS. 7A-E

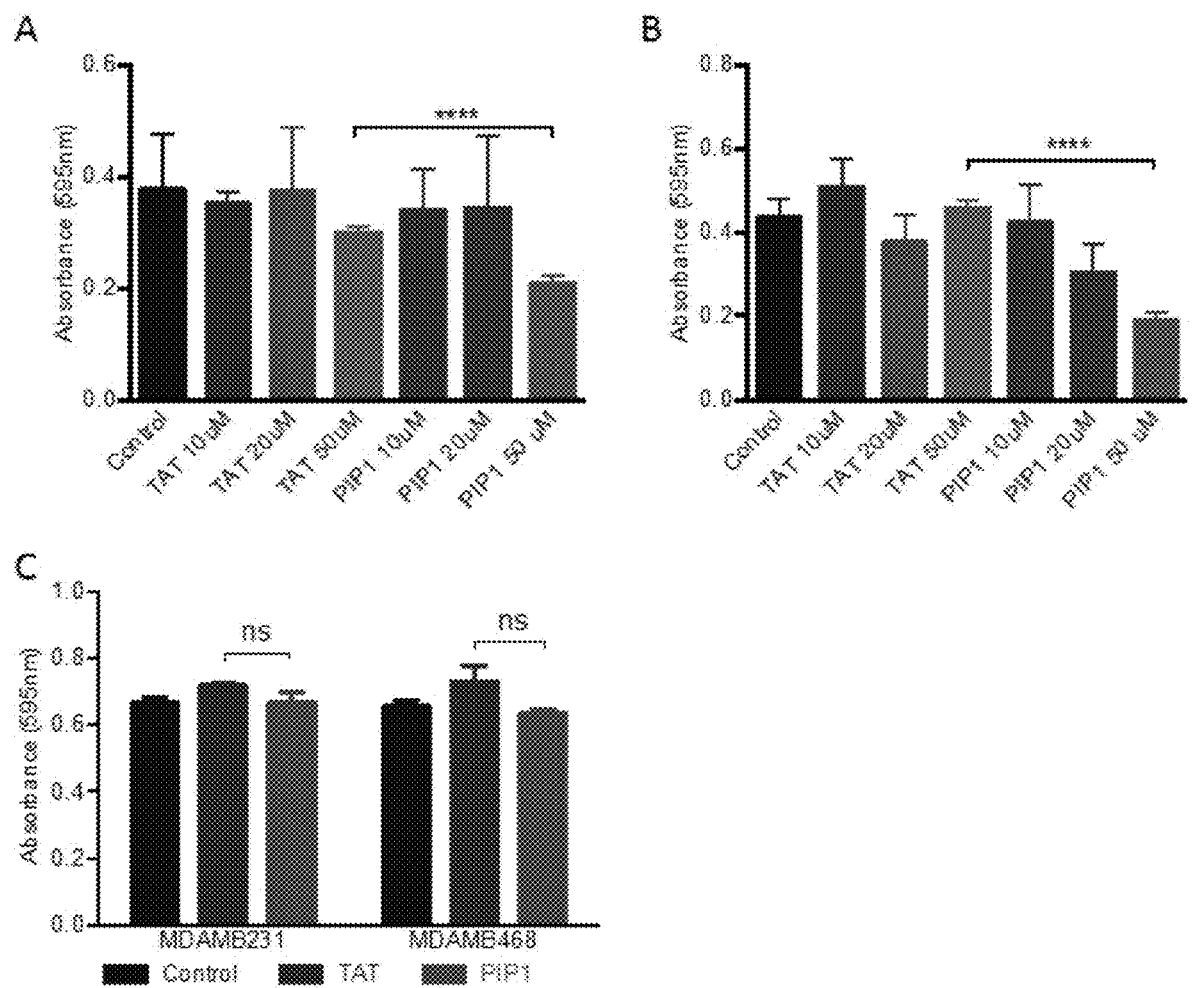
FIGS. 8A-C

FIGS. 13A-C

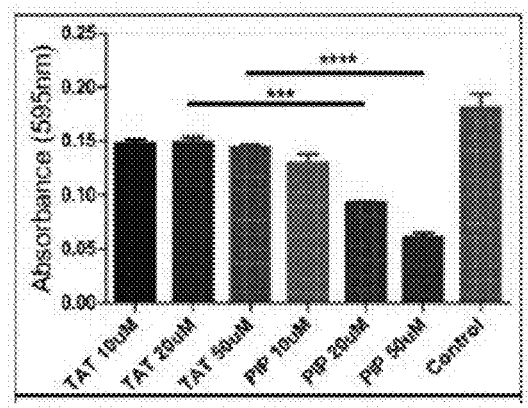
FIG. 14
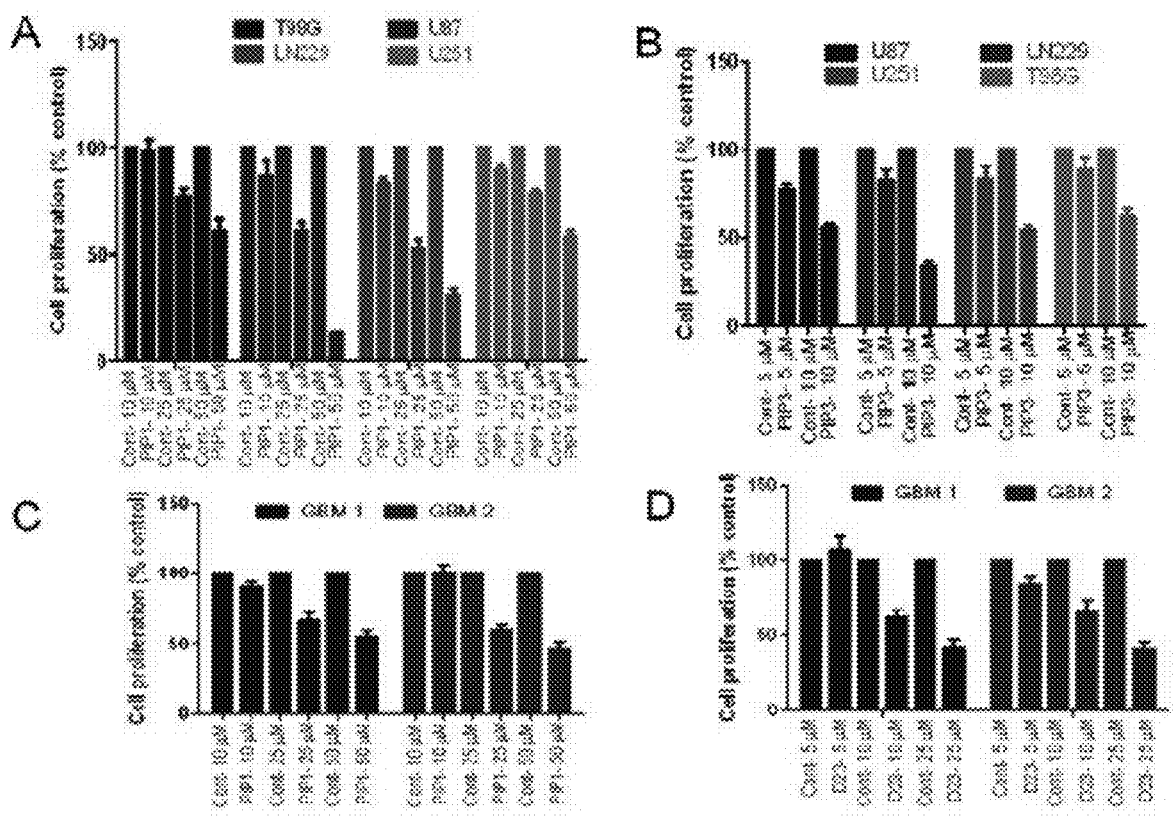
FIGS. 15A-D

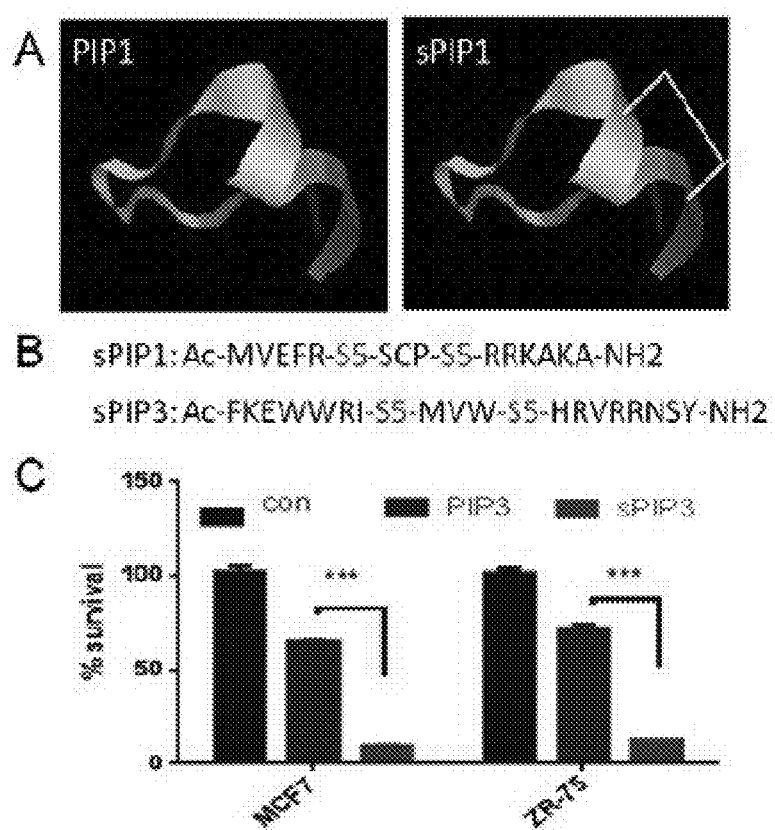
FIGS. 16A-C

SEQUENCE LISTING

```
<160> NUMBER OF SEQ ID NOS: 69

<210> SEQ ID NO 1
<211> LENGTH: 16
<212> TYPE: PRT
<213> ORGANISM: Artificial
<220> FEATURE:
<223> OTHER INFORMATION: Synthetic peptide

<400> SEQUENCE: 1

Met Val Glu Phe Arg Trp Ser Cys Pro Gly Arg Arg Lys Ala Lys Ala
1               5                   10                  15

<210> SEQ ID NO 2
<211> LENGTH: 18
<212> TYPE: PRT
<213> ORGANISM: Artificial
<220> FEATURE:
<223> OTHER INFORMATION: Synthetic peptide

<400> SEQUENCE: 2

Ile Met Gly Arg Gly Leu Cys Met Arg Gly Val Val Arg Gly Arg Gly
1               5                   10                  15

Arg Asn

<210> SEQ ID NO 3
<211> LENGTH: 20
<212> TYPE: PRT
<213> ORGANISM: Artificial
<220> FEATURE:
<223> OTHER INFORMATION: Synthetic peptide

<400> SEQUENCE: 3

Phe Lys Glu Trp Trp Arg Ile Asp Met Val Trp Leu His Arg Val Arg
1               5                   10                  15
```

Arg Asn Ser Tyr
        20

<210> SEQ ID NO 4

<400> SEQUENCE: 4

000

<210> SEQ ID NO 5
<211> LENGTH: 34
<212> TYPE: PRT
<213> ORGANISM: Artificial
<220> FEATURE:
<223> OTHER INFORMATION: Synthetic peptide

<400> SEQUENCE: 5

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Pro
            20                  25                  30

Val Glu

<210> SEQ ID NO 6
<211> LENGTH: 16
<212> TYPE: PRT
<213> ORGANISM: Artificial
<220> FEATURE:
<223> OTHER INFORMATION: Synthetic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 7
<212> TYPE: PRT
<213> ORGANISM: Artificial
<220> FEATURE:
<223> OTHER INFORMATION: Synthetic peptide

<400> SEQUENCE: 7

Arg Arg Met Lys Trp Lys Lys
1               5

<210> SEQ ID NO 8
<211> LENGTH: 16
<212> TYPE: PRT
<213> ORGANISM: Artificial
<220> FEATURE:
<223> OTHER INFORMATION: Synthetic peptide

<400> SEQUENCE: 8

Arg Arg Trp Arg Arg Trp Trp Arg Arg Trp Trp Arg Arg Trp Arg Arg
1               5                   10                  15

<210> SEQ ID NO 9
<211> LENGTH: 18
<212> TYPE: PRT
<213> ORGANISM: Artificial
<220> FEATURE:
<223> OTHER INFORMATION: Synthetic peptide

<400> SEQUENCE: 9

Arg Gly Gly Arg Leu Ser Tyr Ser Arg Arg Arg Phe Ser Thr Ser Thr
1               5                   10                  15

Gly Arg

<210> SEQ ID NO 10
<211> LENGTH: 11
<212> TYPE: PRT
<213> ORGANISM: Artificial
<220> FEATURE:
<223> OTHER INFORMATION: Synthetic peptide

<400> SEQUENCE: 10

Tyr Gly Arg Lys Lys Arg Arg Gln Arg Arg Arg
1               5                   10

<210> SEQ ID NO 11
<211> LENGTH: 9
<212> TYPE: PRT
<213> ORGANISM: Artificial
<220> FEATURE:
<223> OTHER INFORMATION: Synthetic peptide

<400> SEQUENCE: 11

Arg Lys Lys Arg Arg Gln Arg Arg Arg
1               5

<210> SEQ ID NO 12
<211> LENGTH: 11
<212> TYPE: PRT
<213> ORGANISM: Artificial
<220> FEATURE:
<223> OTHER INFORMATION: Synthetic peptide

<400> SEQUENCE: 12

Tyr Ala Arg Ala Ala Ala Arg Gln Ala Arg Ala
1               5                   10

<210> SEQ ID NO 13
<211> LENGTH: 8
<212> TYPE: PRT
<213> ORGANISM: Artificial
<220> FEATURE:
<223> OTHER INFORMATION: Synthetic peptide

<400> SEQUENCE: 13

Arg Arg Arg Arg Arg Arg Arg Arg
1               5

<210> SEQ ID NO 14
<211> LENGTH: 8
<212> TYPE: PRT
<213> ORGANISM: Artificial
<220> FEATURE:
<223> OTHER INFORMATION: Synthetic peptide

<400> SEQUENCE: 14

Lys Lys Lys Lys Lys Lys Lys Lys
1               5

<210> SEQ ID NO 15
<211> LENGTH: 27
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

```
<400> SEQUENCE: 15

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 16
<211> LENGTH: 18
<212> TYPE: PRT
<213> ORGANISM: Artificial
<220> FEATURE:
<223> OTHER INFORMATION: Synthetic peptide

<400> SEQUENCE: 16

Leu Leu Ile Leu Leu Arg Arg Arg Ile Arg Lys Gln Ala Asn Ala His
1               5                   10                  15

Ser Lys

<210> SEQ ID NO 17
<211> LENGTH: 16
<212> TYPE: PRT
<213> ORGANISM: Artificial
<220> FEATURE:
<223> OTHER INFORMATION: Synthetic peptide

<400> SEQUENCE: 17

Ser Arg Arg His His Cys Arg Ser Lys Ala Lys Arg Ser Arg His His
1               5                   10                  15

<210> SEQ ID NO 18
<211> LENGTH: 11
<212> TYPE: PRT
<213> ORGANISM: Artificial
<220> FEATURE:
<223> OTHER INFORMATION: Synthetic peptide

<400> SEQUENCE: 18

Asn Arg Ala Arg Arg Asn Arg Arg Arg Val Arg
1               5                   10

<210> SEQ ID NO 19
<211> LENGTH: 15
<212> TYPE: PRT
<213> ORGANISM: Artificial
<220> FEATURE:
<223> OTHER INFORMATION: Synthetic peptide

<400> SEQUENCE: 19

Arg Gln Leu Arg Ile Ala Gly Arg Arg Leu Arg Gly Arg Ser Arg
1               5                   10                  15

<210> SEQ ID NO 20
<211> LENGTH: 13
<212> TYPE: PRT
<213> ORGANISM: Artificial
<220> FEATURE:
<223> OTHER INFORMATION: Synthetic peptide

<400> SEQUENCE: 20

Lys Leu Ile Lys Gly Arg Thr Pro Ile Lys Phe Gly Lys
1               5                   10

<210> SEQ ID NO 21
<211> LENGTH: 10
```

```
<212> TYPE: PRT
<213> ORGANISM: Artificial
<220> FEATURE:
<223> OTHER INFORMATION: Synthetic peptide

<400> SEQUENCE: 21

Arg Arg Ile Pro Asn Arg Arg Pro Arg Arg
1               5                   10

<210> SEQ ID NO 22
<211> LENGTH: 18
<212> TYPE: PRT
<213> ORGANISM: Artificial
<220> FEATURE:
<223> OTHER INFORMATION: Synthetic peptide

<400> SEQUENCE: 22

Lys Leu Ala Leu Lys Leu Ala Leu Lys Ala Leu Lys Ala Ala Leu Lys
1               5                   10                  15

Leu Ala

<210> SEQ ID NO 23
<211> LENGTH: 14
<212> TYPE: PRT
<213> ORGANISM: Artificial
<220> FEATURE:
<223> OTHER INFORMATION: Synthetic peptide

<400> SEQUENCE: 23

Lys Leu Ala Lys Leu Ala Lys Lys Leu Ala Lys Leu Ala Lys
1               5                   10

<210> SEQ ID NO 24
<211> LENGTH: 27
<212> TYPE: PRT
<213> ORGANISM: Artificial
<220> FEATURE:
<223> OTHER INFORMATION: Synthetic peptide

<400> SEQUENCE: 24

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 25
<211> LENGTH: 21
<212> TYPE: PRT
<213> ORGANISM: Artificial
<220> FEATURE:
<223> OTHER INFORMATION: Synthetic peptide

<400> SEQUENCE: 25

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 26
<211> LENGTH: 23
<212> TYPE: PRT
<213> ORGANISM: Artificial
<220> FEATURE:
<223> OTHER INFORMATION: Synthetic peptide

<400> SEQUENCE: 26
```

```
Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 27
<211> LENGTH: 23
<212> TYPE: PRT
<213> ORGANISM: Artificial
<220> FEATURE:
<223> OTHER INFORMATION: Synthetic peptide

<400> SEQUENCE: 27

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 28
<211> LENGTH: 26
<212> TYPE: PRT
<213> ORGANISM: Artificial
<220> FEATURE:
<223> OTHER INFORMATION: Synthetic peptide

<400> SEQUENCE: 28

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 29
<211> LENGTH: 28
<212> TYPE: PRT
<213> ORGANISM: Artificial
<220> FEATURE:
<223> OTHER INFORMATION: Synthetic peptide

<400> SEQUENCE: 29

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 30
<211> LENGTH: 24
<212> TYPE: PRT
<213> ORGANISM: Artificial
<220> FEATURE:
<223> OTHER INFORMATION: Synthetic peptide

<400> SEQUENCE: 30

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 31
<211> LENGTH: 26
<212> TYPE: PRT
<213> ORGANISM: Artificial
<220> FEATURE:
<223> OTHER INFORMATION: Synthetic peptide
<220> FEATURE:
```

```
<221> NAME/KEY: misc_feature
<222> LOCATION: (24)..(24)
<223> OTHER INFORMATION: Xaa can be any naturally occurring amino acid

<400> SEQUENCE: 31

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25

<210> SEQ ID NO 32
<211> LENGTH: 14
<212> TYPE: PRT
<213> ORGANISM: Artificial
<220> FEATURE:
<223> OTHER INFORMATION: Synthetic peptide

<400> SEQUENCE: 32

Pro Pro Pro Pro Pro Pro Pro Pro Pro Pro Pro Pro Pro Pro
1               5                   10

<210> SEQ ID NO 33
<211> LENGTH: 18
<212> TYPE: PRT
<213> ORGANISM: Artificial
<220> FEATURE:
<223> OTHER INFORMATION: Synthetic peptide

<400> SEQUENCE: 33

Val Arg Leu Pro Pro Pro Val Arg Leu Pro Pro Pro Val Arg Leu Pro
1               5                   10                  15

Pro Pro

<210> SEQ ID NO 34
<211> LENGTH: 10
<212> TYPE: PRT
<213> ORGANISM: Artificial
<220> FEATURE:
<223> OTHER INFORMATION: Synthetic peptide

<400> SEQUENCE: 34

Pro Arg Pro Leu Pro Pro Pro Arg Pro Gly
1               5                   10

<210> SEQ ID NO 35
<211> LENGTH: 30
<212> TYPE: PRT
<213> ORGANISM: Artificial
<220> FEATURE:
<223> OTHER INFORMATION: Synthetic peptide

<400> SEQUENCE: 35

Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 36
<211> LENGTH: 21
<212> TYPE: PRT
<213> ORGANISM: Artificial
<220> FEATURE:
<223> OTHER INFORMATION: Synthetic peptide

<400> SEQUENCE: 36
```

Thr Arg Ser Ser Arg Ala Gly Leu Gln Phe Pro Val Gly Arg Val His
1               5                   10                  15

Arg Leu Leu Arg Lys
            20

<210> SEQ ID NO 37
<211> LENGTH: 23
<212> TYPE: PRT
<213> ORGANISM: Artificial
<220> FEATURE:
<223> OTHER INFORMATION: Synthetic peptide

<400> SEQUENCE: 37

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 38
<211> LENGTH: 37
<212> TYPE: PRT
<213> ORGANISM: Artificial
<220> FEATURE:
<223> OTHER INFORMATION: Synthetic peptide

<400> SEQUENCE: 38

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 39
<211> LENGTH: 28
<212> TYPE: PRT
<213> ORGANISM: Artificial
<220> FEATURE:
<223> OTHER INFORMATION: Synthetic peptide

<400> SEQUENCE: 39

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 40
<211> LENGTH: 26
<212> TYPE: PRT
<213> ORGANISM: Artificial
<220> FEATURE:
<223> OTHER INFORMATION: Synthetic peptide

<400> SEQUENCE: 40

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 41
<211> LENGTH: 14
<212> TYPE: PRT
<213> ORGANISM: Artificial
<220> FEATURE:

```
<223> OTHER INFORMATION: Synthetic peptide

<400> SEQUENCE: 41

Ile Asn Leu Lys Ala Leu Ala Ala Leu Ala Lys Lys Ile Leu
1               5                   10

<210> SEQ ID NO 42
<211> LENGTH: 33
<212> TYPE: PRT
<213> ORGANISM: Artificial
<220> FEATURE:
<223> OTHER INFORMATION: Synthetic peptide

<400> SEQUENCE: 42

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
            20                  25                  30

Glu

<210> SEQ ID NO 43
<211> LENGTH: 15
<212> TYPE: PRT
<213> ORGANISM: Artificial
<220> FEATURE:
<223> OTHER INFORMATION: Synthetic peptide

<400> SEQUENCE: 43

Leu Ala Lys Trp Ala Leu Lys Gln Gly Phe Ala Lys Leu Lys Ser
1               5                   10                  15

<210> SEQ ID NO 44
<211> LENGTH: 27
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 44

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 45
<211> LENGTH: 41
<212> TYPE: PRT
<213> ORGANISM: Artificial
<220> FEATURE:
<223> OTHER INFORMATION: Synthetic peptide

<400> SEQUENCE: 45

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
        35                  40

<210> SEQ ID NO 46
```

```
<211> LENGTH: 20
<212> TYPE: PRT
<213> ORGANISM: Artificial
<220> FEATURE:
<223> OTHER INFORMATION: Synthetic peptide

<400> SEQUENCE: 46

Leu Lys Lys Leu Leu Lys Lys Leu Leu Lys Lys Leu Leu Lys Lys Leu
1               5                   10                  15

Leu Lys Lys Leu
            20

<210> SEQ ID NO 47
<211> LENGTH: 18
<212> TYPE: PRT
<213> ORGANISM: Artificial
<220> FEATURE:
<223> OTHER INFORMATION: Synthetic peptide

<400> SEQUENCE: 47

Lys Leu Lys Leu Lys Leu Lys Leu Lys Leu Lys Leu Lys Leu Lys Leu
1               5                   10                  15

Lys Leu

<210> SEQ ID NO 48
<211> LENGTH: 18
<212> TYPE: PRT
<213> ORGANISM: Artificial
<220> FEATURE:
<223> OTHER INFORMATION: Synthetic peptide

<400> SEQUENCE: 48

Pro Ala Trp Arg Lys Ala Phe Arg Trp Ala Trp Arg Met Leu Lys Lys
1               5                   10                  15

Ala Ala

<210> SEQ ID NO 49
<211> LENGTH: 22
<212> TYPE: DNA
<213> ORGANISM: Artificial
<220> FEATURE:
<223> OTHER INFORMATION: Synthetic oligonucleotide

<400> SEQUENCE: 49
aacagtgttg acatgaagag cc                                          22

<210> SEQ ID NO 50
<211> LENGTH: 22
<212> TYPE: DNA
<213> ORGANISM: Artificial
<220> FEATURE:
<223> OTHER INFORMATION: Synthetic oligonucleotide

<400> SEQUENCE: 50
tgtaaaacag cacgtcatcc tt                                          22

<210> SEQ ID NO 51
<211> LENGTH: 21
<212> TYPE: DNA
<213> ORGANISM: Artificial
<220> FEATURE:
<223> OTHER INFORMATION: Synthetic oligonucleotide

<400> SEQUENCE: 51
ccacctgatg tgtgtgcttt g                                           21
```

<210> SEQ ID NO 52
<211> LENGTH: 22
<212> TYPE: DNA
<213> ORGANISM: Artificial
<220> FEATURE:
<223> OTHER INFORMATION: Synthetic oligonucleotide

<400> SEQUENCE: 52
ttcagtagtg gtctggtctt gt                                    22

<210> SEQ ID NO 53
<211> LENGTH: 21
<212> TYPE: DNA
<213> ORGANISM: Artificial
<220> FEATURE:
<223> OTHER INFORMATION: Synthetic oligonucleotide

<400> SEQUENCE: 53
ctctcgtcag gcttgagttt g                                     21

<210> SEQ ID NO 54
<211> LENGTH: 23
<212> TYPE: DNA
<213> ORGANISM: Artificial
<220> FEATURE:
<223> OTHER INFORMATION: Synthetic oligonucleotide

<400> SEQUENCE: 54
gacatctcat ctaggtcaac tgc                                   23

<210> SEQ ID NO 55
<211> LENGTH: 21
<212> TYPE: DNA
<213> ORGANISM: Artificial
<220> FEATURE:
<223> OTHER INFORMATION: Synthetic oligonucleotide

<400> SEQUENCE: 55
atgtccctgg ctgcttattg c                                     21

<210> SEQ ID NO 56
<211> LENGTH: 21
<212> TYPE: DNA
<213> ORGANISM: Artificial
<220> FEATURE:
<223> OTHER INFORMATION: Synthetic oligonucleotide

<400> SEQUENCE: 56
ccagtgtgtg ccacttttg g                                      21

<210> SEQ ID NO 57
<211> LENGTH: 20
<212> TYPE: DNA
<213> ORGANISM: Artificial
<220> FEATURE:
<223> OTHER INFORMATION: Synthetic oligonucleotide

<400> SEQUENCE: 57
ttgttgtagc tctgggagca                                       20

<210> SEQ ID NO 58
<211> LENGTH: 20
<212> TYPE: DNA
<213> ORGANISM: Artificial
<220> FEATURE:

<223> OTHER INFORMATION: Synthetic oligonucleotide

<400> SEQUENCE: 58
caaccagcca agaggctaag         20

<210> SEQ ID NO 59
<211> LENGTH: 12
<212> TYPE: PRT
<213> ORGANISM: Artificial
<220> FEATURE:
<223> OTHER INFORMATION: Synthetic peptide

<400> SEQUENCE: 59

Gly Arg Lys Lys Arg Arg Gln Arg Arg Arg Gly Gly
1               5                   10

<210> SEQ ID NO 60
<211> LENGTH: 28
<212> TYPE: PRT
<213> ORGANISM: Artificial
<220> FEATURE:
<223> OTHER INFORMATION: Synthetic peptide

<400> SEQUENCE: 60

Gly Arg Lys Lys Arg Arg Gln Arg Arg Arg Gly Gly Met Val Glu Phe
1               5                   10                  15

Arg Trp Ser Cys Pro Gly Arg Arg Lys Ala Lys Ala
            20                  25

<210> SEQ ID NO 61
<211> LENGTH: 30
<212> TYPE: PRT
<213> ORGANISM: Artificial
<220> FEATURE:
<223> OTHER INFORMATION: Synthetic peptide

<400> SEQUENCE: 61

Gly Arg Lys Lys Arg Arg Gln Arg Arg Arg Gly Gly Ile Met Gly Arg
1               5                   10                  15

Gly Leu Cys Met Arg Gly Val Val Arg Gly Arg Gly Arg Asn
            20                  25                  30

<210> SEQ ID NO 62
<211> LENGTH: 32
<212> TYPE: PRT
<213> ORGANISM: Artificial
<220> FEATURE:
<223> OTHER INFORMATION: Synthetic peptide

<400> SEQUENCE: 62

Gly Arg Lys Lys Arg Arg Gln Arg Arg Arg Gly Gly Phe Lys Glu Trp
1               5                   10                  15

Trp Arg Ile Asp Met Val Trp Leu His Arg Val Arg Arg Asn Ser Tyr
            20                  25                  30

<210> SEQ ID NO 63
<211> LENGTH: 5
<212> TYPE: PRT
<213> ORGANISM: Artificial
<220> FEATURE:
<223> OTHER INFORMATION: Synthetic peptide

<400> SEQUENCE: 63

Met Val Glu Phe Arg
1               5

<210> SEQ ID NO 64
<211> LENGTH: 6
<212> TYPE: PRT
<213> ORGANISM: Artificial
<220> FEATURE:
<223> OTHER INFORMATION: Synthetic peptide

<400> SEQUENCE: 64

Arg Arg Lys Ala Lys Ala
1               5

<210> SEQ ID NO 65
<211> LENGTH: 8
<212> TYPE: PRT
<213> ORGANISM: Artificial
<220> FEATURE:
<223> OTHER INFORMATION: Synthetic peptide

<400> SEQUENCE: 65

Pro Gly Arg Arg Lys Ala Lys Ala
1               5

<210> SEQ ID NO 66
<211> LENGTH: 7
<212> TYPE: PRT
<213> ORGANISM: Artificial
<220> FEATURE:
<223> OTHER INFORMATION: Synthetic peptide

<400> SEQUENCE: 66

Phe Lys Glu Trp Trp Arg Ile
1               5

<210> SEQ ID NO 67
<211> LENGTH: 8
<212> TYPE: PRT
<213> ORGANISM: Artificial
<220> FEATURE:
<223> OTHER INFORMATION: Synthetic peptide

<400> SEQUENCE: 67

His Arg Val Arg Arg Asn Ser Tyr
1               5

<210> SEQ ID NO 68
<211> LENGTH: 10
<212> TYPE: PRT
<213> ORGANISM: Artificial
<220> FEATURE:
<223> OTHER INFORMATION: Synthetic peptide

<400> SEQUENCE: 68

Phe Lys Glu Trp Trp Arg Ile Asp Met Val
1               5                   10

<210> SEQ ID NO 69
<211> LENGTH: 5
<212> TYPE: PRT
<213> ORGANISM: Artificial
<220> FEATURE:
<223> OTHER INFORMATION: Synthetic peptide

<400> SEQUENCE: 69

Arg Arg Asn Ser Tyr
1               5

TARGETING OF PELP1 IN CANCER THERAPY

This application claims benefit of priority to U.S. Provisional Application Ser. No. 61/927,743, filed Jan. 15, 2014, the entire contents of which are hereby incorporated by reference.

GOVERNMENT SUPPORT CLAUSE

This application is a national phase application under 35 U.S.C. § 371 of International Application No. PCT/US2015/011377, filed Jan. 14, 2015, which claims benefit of priority to U.S. Provisional Application Ser. No. 61/927,743, filed Jan. 15, 2014, the entire contents of each of the above-referenced disclosures are hereby incorporated by reference.

Pursuant to 37 C.F.R. 1.821(c), a sequence listing is submitted herewith as an ASCII compliant text file named "HSCSP0011US_ST25.txt", created on Jul. 7, 2016 and having a size of 18 kilobytes. The content of the aforementioned file is hereby incorporated by reference in its entirety.

BACKGROUND

1. Field of the Invention

This disclosure relates to the fields of medicine, pathology, molecular biology and onocology. In particular, peptides have been identified that inhibit PELP1 interactions with molecules that lead to oncogenic signaling. The use of such peptides in treating cancers is also disclosed.

2. Related Art

Endocrine therapy for breast cancer patients targets the estrogen receptor alpha (ERα) with either antiestrogens or aromatase inhibitors (Osborne, 1998; Harvey et al., 1999). Although hormonal therapy targeting ERα is effective for the treatment of breast cancer, a significant number of patients develop resistance leading to metastatic disease. These tumors still have ERα signaling including several oncogenic ERα coregulators that are upregulated and promote breast cancer therapy resistance and metastasis; therefore, targeting these coregulators could be a promising cancer therapeutic (Bekri et al., 1997; Habashy et al., 2010). Current therapeutic approaches are ineffective in targeting oncogenic coregulators that are involved in therapy resistance. Cancer stem cells (CSCs) may also play a role in therapy resistance, and therefore therapies must completely eradicate the CSCs to be effective.

One coactivator of ERα that is known to be upregulated in breast cancer, promote therapy resistance and metastasis, and provide cancer cells with a distinct growth and survival advantage is proline-, glutamic acid-, and leucine-rich protein 1 (PELP1) (Rajhans et al., 2007; Girard et al., 2013; Vadlamudi et al., 2001; 2007; Nair et al., 2010a). PELP1 overexpression results in cellular transformation, anchorage-independence and tumor growth in xenograft studies and is linked to shorter breast cancer specific survival (Habashy et al., 2010; Rajhans et al., 2007). In invasive breast cancers, PELP1 localizes to the cytoplasm and correlates with increased resistance to tamoxifen treatment (Kumar et al., 2009). PELP1 has several protein-protein interactions that play a central role in breast cancer progression (Nair et al., 2011; Vallabhaneni et al., 2011; Cortez et al., 2012). Inhibition of PELP1 with siRNA liposomes reduces tumor growth in a breast cancer xenograft model, suggesting that PELP1 is a promising potential therapeutic target (Cortez et al., 2012).

Estrogen signaling contributes to epigenetic changes through the induction of histone modifications at ERα target gene promoters which play a role in the regulation of transcription (Mann et al., 2011). The methylation of histone tails can have distinct effects on transcription depending on the chromosomal location, the combination of posttranslational modifications, and the enzyme involved in the particular modification (Nishioka et al., 2002). PELP1 couples ERα with epigenetic modifiers at target genes and recognizes histone demethylation (Mann et al., 2013). The epigenetic modifier G9a is a SET domain-containing lysine methyltransferase that transfers methyl groups to the lysine residues 9 and 27 of histones with a 10-20 fold higher activity than Suv39h1 (Tachibana et al., 2001). G9a is mainly responsible for monomethylation and dimethylation of H3K9 and contains ankyrin repeats, which may be involved in intracellular protein-protein interactions (Milner et al., 1993; Brown et al., 2001). These ankyrin repeat domains bind with strong preference to N-terminal H3 peptides containing mono- or dimethyl K9, making it a methyltransferase that generates and reads the same epigenetic mark (Collins et al., 2008). G9a functions as a coregulator of ERα and overexpression induces an invasive cancer phenotype (Purcell et al., 2011; Kondo et al., 2008; Chen et al., 2010). Inhibition of G9a with small molecules has the potential to be an effective therapeutic for cancer (Kubicek et al., 2007; Liu et al., 2009). Although these studies implicate PELP1 and G9a signaling as playing a role in breast cancer, it is unknown whether these pathways coordinately influence breast cancer progression and therapy resistance, or whether targeting this interaction would provide any beneficial effect.

SUMMARY

Thus, in accordance with the present disclosure, there is provided a method of inhibiting a cancer cell in a subject comprising administering to said subject a peptide or peptoid that binds to PELP1. The peptide or peptoid may comprise at least 5, 6, 7, 8, 9, 10, 15, 20, 25, 30, 35, 40, 45 or 50 residues. The peptide or peptoid may contain no more than 10, 11, 12, 13, 14, 15, 16, 17, 18, 19, 20, 25, 30, 35, 40, 45 or 50 residues. The peptide or peptoid may be fused to a cell delivery domain, such as TAT. The peptide may comprise all L amino acids, all D amino acids, or a mix of L and D amino acids. The peptide may be a stapled peptide. The peptide may comprise a bridge, such as a bridge comprising a linker, chemically modified side chains, or hydrocarbon stapling. The linker may comprise a modification that stabilizes an alpha-helical structure of said peptide. The peptide may comprise the sequence MVEFRWSCPGRRKAKA (SEQ ID NO: 1), IMGRGLCMRGVVRGRGRN (SEQ ID NO: 2) or FKEWWRIDMVWLHRVRRNSY (SEQ ID NO: 3), and may consist or consist essentially of the sequence GRKKRRQRRRGGMVEFRWSCPGRRKAKA (SEQ ID NO: 60), GRKKRRQRRRGGIMGRGLCMRGVVRGRGRN (SEQ ID NO: 61) or GRKKRRQRRRGGFKEWWRIDMVWLHRVRRNSY (SEQ ID NO: 62).

The cancer cell may be is a prostate, breast, glioma or ovarian cancer cell. Administering may comprise intravenous, intra-arterial, intra-tumoral, subcutaneous, topical or intraperitoneal administration or local, regional, systemic, or continual administration. Inhibiting may comprise inducing growth arrest of said tumor cell, apoptosis of said tumor cell and/or necrosis of a tumor tissue comprising said tumor cell. The method may further comprise administering to said subject a second anti-cancer therapy. The second anti-cancer therapy may be surgery, chemotherapy, radiotherapy, hormonal therapy, toxin therapy, immunotherapy, and cryotherapy. The second anti-cancer therapy may be administered prior to said peptide or peptoid, after said peptide or peptoid or at the same time as said peptide or peptoid. The subject may be a human. The peptide or peptoid may be administered at 0.1-500 mg/kg/d, or at 10-100 mg/kg/d. The peptide or peptoid may be administered daily, such as daily for 7 days, 2 weeks, 3 weeks, 4 weeks, one month, 6 weeks, 8 weeks, two months, 12 weeks, or 3 months. The peptide or peptoid may be administered weekly, such as weekly for 2 weeks, 3 weeks, 4 weeks, 6 weeks, 8 weeks, 10 weeks, or 12 weeks. The peptide or peptoid may inhibit estrogen receptor co-activation functions of PELP1. The estrogen receptor co-activator function may comprise PELP1 binding to histone lysine methyltransferase G9a. The breast cancer cell may be a triple negative breast cancer cell.

Also provided is a pharmaceutical composition comprising (a) a peptide or peptoid that binds to PELP1 and blocks one or more estrogen receptor co-activation functions of PELP1 and (b) a pharmaceutically acceptable carrier, buffer or diluent. The peptide or peptoid may comprises at least 5, 6, 7, 8, 9, 10, 15, 20, 25, 30, 35, 40, 45 or 50 residues. The peptide or peptoid may contain no more than 10, 11, 12, 13, 14, 15, 16, 17, 18, 19, 20, 25, 30, 35, 40, 45 or 50 residues. The peptide or peptoid is fused to a cell delivery domain, such as TAT. The peptide may comprise all L amino acids, all D amino acids, or a mix of L and D amino acids. The peptide may be a stapled peptide. The peptide may comprise a bridge, such as a bridge comprising a linker, chemically modified side chains, or hydrocarbon stapling. The linker may comprise a modification that stabilizes an alpha-helical structure of said peptide. The peptide may comprise the sequence MVEFRWSCPGRRKAKA (SEQ ID NO: 1), IMGRGLCMRGVVRGRGRN (SEQ ID NO: 2) or FKEWWRIDMVWLHRVRRNSY (SEQ ID NO: 3), or consists or consists essentially of the sequence GRKKRRQRRRGGM-VEFRWSCPGRRKAKA (SEQ ID NO: 60), GRKKRRQR-RRGGIMGRGLCMRGVVRGRGRN (SEQ ID NO: 61) or GRKKRRQRRRGGFKEWWRIDMVWLHRVRRNSY (SEQ ID NO: 62).

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawings will be provided by the Office upon request and payment of the necessary fee.

FIGS. 1A-D. (FIG. 1A) Diagram for yeast two hybrid screen to identify PELP1 binding peptides. Four regions of PELP1 were tagged with the binding domain and a library of $10^6$ random peptides (Clontech) were bound to an activation domain. The number of positive colonies per region of PELP1 are shown in the graph. (FIG. 1B) A proliferation assay was performed with ZRPELP1 cells plated in a 96 well plate, treated with peptide every 3 days and absorbance was measured at 7 days. (FIG. 1C) ZR75 were plated in a 6-well plate on coverslips in 8% RPMI and treated with 10 uM FITC labeled peptide for 30, 60, or 120 minutes. They were then fixed with pararformaldehyde, stained for PELP1 (red) and DAPI (blue), and imaged by confocal microscopy to monitor intracellular delivery. (FIG. 1D) ZR75 cells were starved of estrogen for 72 hours and treated with estradiol $10^{-7}$ M for 12 hours. Nuclear lysate was incubated with biotin-tagged peptides bound to avidin beads for one hour. Beads were washed, run on SDS-PAGE gel and probed for PELP1 expression. Input of nuclear lysate is shown as control.

FIGS. 2A-D. (FIG. 2A) Immunoprecipitation was performed on nuclear lysates obtained from ZRPELP1 cells grown in 5% DCC for 72 hours and treated with estradiol $10^{-7}$ M for 12 hours. PELP1 was immunoprecipitated and western blotting was performed for PELP1 and G9a expression with IgG as the control. (FIG. 2B) Various fragments of PELP1 bound to glutathione beads were incubated with recombinant G9a for 2 hours. Beads were washed, run on an SDS-PAGE gel and immunoblotted for G9a expression. GST tag alone is shown as control. (FIG. 2C) Recombinant G9a-GST was bound to glutathione beads and incubated with purified PELP1 and peptides for 2 hours. Beads were washed and run on SDS-PAGE gel. (FIG. 2D) ZR75 cells were transfected with ERE-luciferase, PELP1 and/or G9a plasmids and treated with peptide for 24 hours and estradiol $10^{-7}$ M for 12 hours. Relative luciferase activity is shown.

FIGS. 3A-F. (FIG. 3A) Recombinant histones were incubated with G9a with increasing concentrations of PELP1, incubated 1 hour at 30° C. and western blot analysis was performed for expression of H3K9me2. Total histone H3 is shown as the control. (FIG. 3B) qRTPCR analysis of ZR75 and ZRPELP1KD cells treated with 10 μM TAT or PIP1 for 24 hours. G9a target genes PECAM1, SERAC1, RB1 and BMI1 expression is shown as—fold change over actin. (FIG. 3B) ChIP-sequencing location analysis of H3K9me2 in control ZR75 model cells. (FIG. 3D) ChIP-sequencing location analysis of H3K9me2 in stable ZR75PELP1KD cells. (FIG. 3E) Ingenuity pathway analysis of genes from binding peaks of ChIP-sequencing of H3K9me2 in stable PELP1 ZR75PELP1KD cells. (FIG. 3F) Image from Integrated Genome Viewer of ChIP-sequencing of H3K9me2 in ZR75 and ZRPELP1KD cells.

FIGS. 4A-E. (FIG. 4A) ZR75vec, ZR75PELP1, MCF7vec and MCF7PELP1 cells were treated in triplicate with TAT, PIP1 or PIP1 deletions (Del1, Del2, Del3) at 10 uM every 3 days and proliferation was measured by MTT assay on day 7. (FIG. 4B) ZRPELP1 cells were transfected with ERE-luciferase and treated with TAT, PIP1, or PIP2 for 24 hours and with estradiol for 12 hours. Relative luciferase activity was measured in triplicate. (FIG. 4C) ZR75 cells were grown in 5% DCC media for 72 hours, treated with TAT or PIP1 every 3 days, and treated with estradiol $10^{-7}$ M for 12 hours. Proliferation was measured in triplicate on day 7 by MTT assay at 595 nm. (FIG. 4D) MCF7-Letrozole resistant cells were grown in 5% DCC media for 72 hours, treated with TAT, PIP1 or PIP2 every 3 days, and letrozole or estradiol $10^{-7}$ M for 12 hours. Proliferation was measured in triplicate on day 7 by MTT assay at 595 nm. (FIG. 4E) MCF7-Tamoxiefn resistant cells were grown in 5% DCC media for 72 hours, treated with TAT, PIP1 or PIP2 every 3 days, and tamoxifen or estradiol $10^{-7}$ M for 12 hours. Proliferation was measured in triplicate on day 7 by MTT assay at 595 nm.

FIGS. 5A-D. (FIG. 5A) ZR75vec, ZR75PELP1, MCF7vec and MCF7PELP1 cells were plated in the top of a Boyden chamber transwell, treated with TAT, PIP1 or PIP2 (10 μM) and absorbance was measured at 12 hours in triplicate. (FIG. 5B) MCF7vec, MCFP7ELP1, ZR75vec and ZR75PELP1 cells were treated in triplicate with TAT, PIP1 or PIP2 (10 μM) every 3 days, fixed with methanol on day 10 and stained with crystal violet. Average colonies per well are shown. (FIG. 5C) ZR75vec and ZR75PELP1 cells were plated in triplicate in agar with 8% RPMI with TAT, PIP1 or PIP2 (10 μM). Colonies were counted on day 14, representative images are shown on right. (FIG. 5D) ZR75 cells were plated on coverslips in triplicate and treated with TAT or PIP1 (10 μM) for 24 hours. Cells were fixed with paraformaldehyde and labeled with TUNEL and DAPI, representative images are shown on right.

FIGS. 6A-C. (FIG. 6A) ZR75, ZR75PELP1 and ZR75PELP1KD cells were FACS sorted for CD44-APC and CD24-PE, and quantification of percentage of CD44high/CD24low cells is shown. (FIG. 6B) MCF7PELP1 cells were FACS sorted for CD44high/CD24low cells and plated in triplicate in serum free mammosphere media with TAT or PIP1 in various concentrations. Mammospheres were counted and imaged on day 7. Representative images are shown on right. (FIG. 6C) Mammospheres from previous assay (C) were dissociated and replated in serum free mammosphere media. Mammospheres were counted and imaged on day 7. Representative images are shown on right.

FIGS. 7A-E. (FIG. 7A) Bacterial purified PELP1 was incubated with biotin-tagged peptides bound to avidin beads for one hour. Beads were washed, run on SDS-PAGE gel and probed for PELP1 expression. Input of bacterial PELP1 is shown as control. (FIG. 7B) Recombinant G9a-GST was bound to glutathione beads and incubated with purified PELP1 and peptides for 2 hours. Beads were washed and run on SDS-PAGE gel. (+2 μM, ++5 μM, +++10 μM). (FIG. 7C) ZRGST and ZRPELP1GST cells were transfected in triplicate with TopFlash β-catenin reporter and treated with TAT or PIP1 (10 μM) for 24 hours. Relative luciferase activity is shown. (FIG. 7D) MCF7vec and MCF7PELP1 cells were treated with TAT or PIP1 (10 μM) and toxicity was measured by CytoTox-Flour Cytotoxicity Assay. (FIG. 7E) ZR75 and ZR75PELP1 cells were treated with TAT, PIP1 or PIP2 for 24 hours and immunoblotted for PELP1 and ERα expression with actin as the loading control.

FIGS. 8A-C. (FIG. 8A) ZR75PELP1KD cells were treated in triplicate with TAT or PIP1 (10, 20, or 50 μM) every 3 days and proliferation was measured by MTT assay on day 7. (FIG. 8B) MCF7PELP1KD cells were treated in triplicate with TAT or PIP1 (10, 20, or 50 μM) every 3 days and proliferation was measured by MTT assay on day 7. (FIG. 8C) MDAMB231 and MDAMB468 cells were treated in triplicate with TAT or PIP1 (10 μM) every 3 days and proliferation was measured by MTT assay on day 7.

(FIG. 13A) Breast cancer cells were treated with vehicle or 10 μM PIP3 and proliferation was measured by using the MTT assay. (FIGS. 13B-C) Dose response curves for PIP3.

FIG. 14. PIP1 inhibits proliferation of ovarian cancer cells.

FIGS. 15A-D. PIPs inhibit proliferation of glioma cells. (FIGS. 15A-B) T98G, LN229 and U251 glioma cells were treated with vehicle or varying concentration of PIP1 or PIP3, and proliferation was measured by using the MTT assay. (FIGS. 15C-D) Patient-derived primary GBM cells were treated with PIP1 or PIP3 and proliferation was measured using the MTT assay.

FIGS. 16A-C. Generation of stapled PIPs. (FIG. 16A) Schematic representation of PIP1 and stapled PIP1 (sPIP1). (FIG. 16B) Sequences of stapled peptides sPIP1, sPIP3, S5 indicated location of staple in the peptide. (FIG. 16C) Breast cancer cells MCF7 and ZR75 were treated with 7.5 μM of PIP3 or sPIP3 and proliferation was measured by using the MTT assay.

DESCRIPTION OF ILLUSTRATIVE EMBODIMENTS

Figure 9:
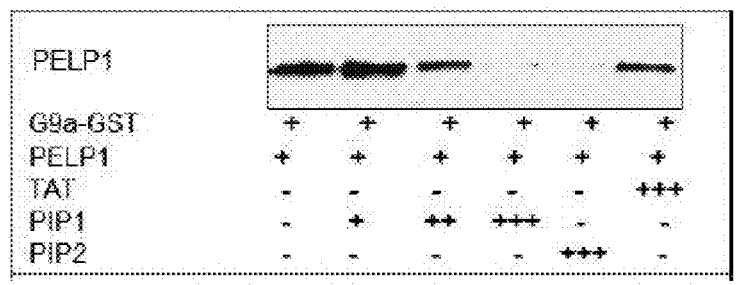
FIG. 9. Peptide competition assay. Recombination G9a was bound to glutathione beads and incubated with purified PELP1 and peptides for 2 hours. Beads were washed and run on SDS-PAGE gel. +2 μM, ++5 μM, +++10 μM.

In the studies described below, the inventors investigated the feasibility of developing inhibitors that effectively block the oncogenic PELP1 signaling that plays a critical role in breast cancer progression. Since PELP1 functions as a scaffolding protein to couple ERα with downstream effector proteins, they reasoned that small peptides that tightly bind to PELP1 (PIPs) will interfere with its critical oncogenic interaction with downstream epigenetic modifiers of ERα signaling. The inventors rationally screened a random peptide library composed of 10 million peptides, identified PELP1 tight-binding peptides that interfere with PELP1 mediated oncogenic functions and developed them as novel cell permeable Peptide Inhibitors of PELP1 (PIPs). They have further developed peptoids modeled off of these sequences that also have inhibitory activity. Their findings revealed that PIPs significantly reduce PELP1-mediated oncogenic functions and inhibit self-renewal of breast cancer stem cells, thus representing a novel class of drugs for curbing breast cancer progression.

These and other aspects of the disclosure are described in greater detail below.

I. PELP1

PELP1 (MNAR) is a transcriptional corepressor for nuclear receptors such as glucocorticoid receptors and a coactivator for estrogen receptors. PELP1 has been shown to bind to both estrogen receptor alpha and estrogen receptor beta. It was also reported that protein tyrosine kinases of the src family can form a complex with estrogen receptors and PELP1 and it was reported that when bound to PELP1 and estrogen receptor alpha the kinase activity of SRC was activated in an estrogen-sensitive manner. Mitogen-activated protein kinases ERK1 and ERK2 were found to become phosphorylated in estrogen-treated cells containing PELP1. It was reported that the enhancement of estrogen-induced gene transcription due to PELP1 could be blocked by protein kinase inhibitors. This suggested a model of PELP1 function in which estrogen and PELP1 cooperate to activate protein kinases which in turn activate gene transcription. When functioning as a corepressor of transcription, PELP1 recruits histone deacetylase. Estrogen has been associated with stimulation of cell proliferation and progression of cells through $G_1$ to the S phase of the cell cycle. The retinoblastoma protein (Rb) is a regulator of $G_1$. It was reported that PELP1 interacts with Rb. It is not known if estrogen receptors can displace histone deacetylase from Rb.

II. PELP-1 PEPTIDES

A. Structure

The present invention contemplates the use of various peptides. In general, the peptides will be 50 residues or less. The overall length may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 4-50 residues, 7-50 residues, 4-25 residues 7-25, residues, 4-20 residues, 7-20 residues, and 3-15 residues, and 7-15 residues are contemplated. The present invention may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

As mentioned above, the present invention contemplates fusing or conjugating a cell pentrating domain (also called a cell delivery domain, or cell transduction domain). Such domains are well known in the art and are generally characterized as short amphipathic or cationic peptides and peptide derivatives, often containing multiple lysine and arginine resides (Fischer, 2007). Of particular interest are the TAT sequence from HIV1 (GRKKRRQRRRGG; SEQ ID NO: 59), and poly-D-Arg and poly-D-Lys sequences (e.g., dextrorotary residues, eight residues in length). Other cell delivery domains are shown in the table below.

TABLE 1

| CPP/CTD PEPTIDES | SEQ ID NO |
|---|---|
| QAATATRGRSAASRPTERPRAPARSASRPRRPVE | 5 |
| RQIKIWFQNRRMKWKK | 6 |
| RRMKWKK | 7 |
| RRWRRWWRRWWRRWRR | 8 |
| RGGRLSYSRRRFSTSTGR | 9 |
| YGRKKRRQRRR | 10 |
| RKKRRQRRR | 11 |
| YARAAARQARA | 12 |
| RRRRRRRR | 13 |
| KKKKKKKK | 14 |
| GWTLNSAGYLLGKINLKALAALAKXIL | 15 |
| LLILLRRRIRKQANAHSK | 16 |
| SRRHHCRSKAKRSRHH | 17 |
| NRARRNRRRVR | 18 |
| RQLRIAGRRLRGRSR | 19 |
| KLIKGRTPIKFGK | 20 |
| RRIPNRRPRR | 21 |
| KLALKLALKALKAALKLA | 22 |
| KLAKLAKKLAKLAK | 23 |
| GALFLGFLGAAGSTNGAWSQPKKKRKV | 24 |
| KETWWETWWTEWSQPKKKRKV | 25 |
| GALFLGWLGAAGSTMGAKKKRKV | 26 |
| MGLGLHLLVLAAALQGAKSKRKV | 27 |
| AAVALLPAVLLALLAPAAANYKKPKL | 28 |
| MANLGYWLLALFVTMWTDVGLCKKRPKP | 29 |
| LGTYTQDFNKFHTFPQTAIGVGAP | 30 |
| DPKGDPKGVTVTVTVTVTGKGDPXPD | 31 |
| PPPPPPPPPPPPPP | 32 |
| VRLPPPVRLPPPVRLPPP | 33 |
| PRPLPPPRPG | 34 |

TABLE 1-continued

| CPP/CTD PEPTIDES | SEQ ID NO |
|---|---|
| SVRRRPRPPYLPRPRPPPFFPPRLPPRIPP | 35 |
| TRSSRAGLQFPVGRVHRLLRK | 36 |
| GIGKFLHSAKKFGKAFVGEIMNS | 37 |
| KWKLFKKIEKVGQNIRDGIIKAGPAVAVVGQATQIAK | 38 |
| ALWMTLLKKVLKAAAKAALNAVLVGANA | 39 |
| GIGAVLKVLTTGLPALISWIKRKRQQ | 40 |
| INLKALAALAKKIL | 41 |
| GFFALIPKIISSPLPKTLLSAVGSALGGSGGQE | 42 |
| LAKWALKQGFAKLKS | 43 |
| SMAQDIISTIGDLVKWIIQTVNXFTKK | 44 |
| LLGDFFRKSKEKIGKEFKRIVQRIKQRIKDFLANLVPRTES | 45 |
| LKKLLKKLLKKLLKKLLKKL | 46 |
| KLKLKLKLKLKLKLKLKL | 47 |
| PAWRKAFRWAWRMLKKAA | 48 |

Also as mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino and/or carboxyl terminal residues.

B. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the twenty standard amino acids can can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Linkers

Linkers or cross-linking agents may be used to fuse peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterofunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

D. Mimetics

In addition to the peptides disclosed herein, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the invention also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention (e.g., Cohen et al., 1990; Navia et al., 1992), the disclosures of which are incorporated herein by reference in their entirety). All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-Ray Crystallography.

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules (Weber, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5.0-7.5. Other additives can include 0.1 M Hepes, 2-4% butanol, 20-100 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer. Proteins to be crystallized can be modified, e.g., by phosphorylation or by using a phosphate mimic (e.g., tungstate, cacodylate, or sulfate).

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique (McPherson, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to between −220° C. and −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film or a detector plate, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. Application No. 2005/0015232, U.S. Pat. No. 6,093,573 and International Application Nos. PCT/

US99/18441, PCT/US99/11913, and PCT/US00/03745. The disclosures of all these patent documents are incorporated herein by reference in their entirety.

NMR Spectroscopy.

Whereas x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa (Wider, 2000).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3-or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, (1996); Gronenborn et al. (1990); and Wider (2000), supra., the disclosures of all of which are incorporated herein by reference in their entirety Also of interest are peptidomimetic compounds that are designed based upon the amino acid sequences of compounds of the invention that are peptides. Peptidomimetic compounds are synthetic compounds having a three-dimensional conformation "motif" that is substantially the same as the three-dimensional conformation of a selected peptide. The peptide motif provides the peptidomimetic compound with the ability to inhibit the oligomerization of MUC1. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

E. Stabilized Peptides

A particular modification is in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge that physically constrains the peptide into its native α-helical shape. In addition to helping retain the native structure needed to interact with a target molecule, this conformation also provides stability against peptidases as well as promotes cell-permeating properties.

More particularly, the term "peptide stapling" may encompasses the joining of two double bond-containing sidechains, two triple bond-containing sidechains, or one double bond-containing and one triple bond-containing side chain, which may be present in a polypeptide chain, using any number of reaction conditions and/or catalysts to facilitate such a reaction, to provide a singly "stapled" polypeptide. In a specific embodiment, the introduction of a staple entails a modification of standard peptide synthesis, with α-methy, α-alkenyl amino acids being introduced at two positions along the peptide chain, separated by either three or six intervening residues (i+4 or i+7). These spacings place the stapling amino acids on the same face of the α-helix, straddling either one (i+4) or two (i+7) helical turns. The fully elongated, resin-bound peptide can be exposed to a ruthenium catalyst that promotes cross-linking of the alkenyl chains through olefin metathesis, thereby forming an all-hydrocarbon macrocyclic cross-link. U.S. Pat. Nos. 7,192,713 and 7,183,059, and U.S. Patent Publications 2005/02506890 and 2006/0008848, describing this technology, are hereby incorporated by reference. See also Schafmeister et al., *Journal of the American Chemical Society,* 122(24): p. 5891-5892 (2000); Walensky et al., *Science* 305:1466-1470 (2004). Additionally, the term "peptide stitching" refers to multiple and tandem "stapling" events in a single peptide chain to provide a "stitched" (multiply stapled) polypeptide, each of which is incorporated herein by reference. See WO 2008/121767 for a specific example of stitched peptide technology.

F. Peptoids

Peptoids, or poly-N-substituted glycines, are a class of peptidomimetics whose side chains are appended to the nitrogen atom of the peptide backbone, rather than to the α-carbons (as they are in amino acids). In peptoids the side chain is connected to the nitrogen of the peptide backbone, instead of the α-carbon as in peptides. Notably, peptoids lack the amide hydrogen which is responsible for many of the secondary structure elements in peptides and proteins. Peptoids were first invented by Reyna J. Simon, Paul Bartlett and Daniel V. Santi to mimic protein/peptide products to aid in the discovery of protease-stable small molecule drugs.

Following the sub-monomer protocol originally created by Zuckermann, each residue is installed in two steps: acylation and displacement. In the acylation step a haloacetic acid, typically bromoacetic acid activated by diisopropylcarbodiimide reacts with the amine of the previous residue. In the displacement step (a classical $S_N2$ reaction), an amine displaces the halide to form the N-substituted glycine residue. The submonomer approach allows the use of any commercially available or synthetically accessible amine with great potential for combinatorial chemistry.

Like D-Peptides and β peptides peptoids are completely resistant to proteolysis, and are therefore advantageous for therapeutic applications where proteolysis is a major issue. Since secondary structure in peptoids does not involve hydrogen bonding, it is not typically denatured by solvent, temperature, or chemical denaturants such as urea (see details below).

Notably, since the amino portion of the amino acid results from the use of any amine, thousands of commercially available amines can be used to generate unprecedented chemical diversity at each position at costs far lower than would be required for similar peptides or peptidomimetics. To date, at least 230 different amines have been used as side chains in peptoids.

Peptoid oligomers are known to be conformationally unstable, due to the flexibility of the main-chain methylene groups and the absence of stabilizing hydrogen bond interactions along the backbone. Nevertheless, through the choice of appropriate side chains it is possible to form specific steric or electronic interactions that favour the formation of stable secondary structures like helices, especially peptoids with C-α-branched side chains are known to adopt structure analogous to polyproline I helix. Different strategies have been employed to predict and characterize peptoid secondary structure, with the ultimate goal of developing fully folded peptoid protein structures. The cis/trans amide bond isomerization still leads to a conformational heterogeneity which doesn't allow for the formation of homogeneous peptoid foldamers. Nonetheless scientists were able to find trans-inducer N-Aryl side chains promoting polyproline type II helix, and strong cis-inducer such as bulky naphtylethyl and tert-butyl side chains. It was also found that $n \rightarrow \pi^*$ interactions can modulate the ratio of cis/trans amide bond conformers, until reaching a complete control of the cis conformer in the peptoid backbone using a functionalizable triazolium side chain.

III. THERAPIES

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Methods of Treatment

Cancer, known medically as a malignant neoplasm, is a broad group of diseases involving unregulated cell growth. In cancer, cells divide and grow uncontrollably, forming malignant tumors, and invading nearby parts of the body. The cancer may also spread to more distant parts of the body through the lymphatic system or bloodstream. Not all tumors are cancerous; benign tumors do not invade neighboring tissues and do not spread throughout the body. There are over 200 different known cancers that affect humans.

The causes of cancer are diverse, complex, and only partially understood. Many things are known to increase the risk of cancer, including tobacco use, dietary factors, certain infections, exposure to radiation, lack of physical activity, obesity, and environmental pollutants. These factors can directly damage genes or combine with existing genetic faults within cells to cause cancerous mutations. Approximately 5-10% of cancers can be traced directly to inherited genetic defects. Many cancers could be prevented by not smoking, eating more vegetables, fruits and whole grains, eating less meat and refined carbohydrates, maintaining a healthy weight, exercising, minimizing sunlight exposure, and being vaccinated against some infectious diseases.

Cancer can be detected in a number of ways, including the presence of certain signs and symptoms, screening tests, or medical imaging. Once a possible cancer is detected it is diagnosed by microscopic examination of a tissue sample. Cancer is usually treated with chemotherapy, radiation therapy and surgery. The chances of surviving the disease vary greatly by the type and location of the cancer and the extent of disease at the start of treatment. While cancer can affect people of all ages, and a few types of cancer are more common in children, the risk of developing cancer generally increases with age. In 2007, cancer caused about 13% of all human deaths worldwide (7.9 million). Rates are rising as more people live to an old age and as mass lifestyle changes occur in the developing world.

The present disclosure thus addresses the treatment of cancer. The types of cancer that may be treated are only limited by the involvement of PELP1. Thus, a wide variety of tumors are contemplated as being treatable including cancers of the brain, lung, liver, spleen, kidney, lymph node, pancreas, small intestine, blood cells, colon, stomach, breast, endometrium, prostate, testicle, cervix, uterus, rectum, eye, ovary, skin, head and neck, esophagus, bone marrow, blood or other tissue.

The dosage of the peptide required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

1. Breast Cancer

Breast cancer refers to cancers originating from breast tissue, most commonly from the inner lining of milk ducts or the lobules that supply the ducts with milk. Cancers originating from ducts are known as ductal carcinomas; those originating from lobules are known as lobular carcinomas. There are many different types of breast cancer, with different stages (spread), aggressiveness, and genetic makeup; survival varies greatly depending on those factors. Computerized models are available to predict survival. With best treatment and dependent on staging, 10-year disease-free survival varies from 98% to 10%. Treatment includes surgery, drugs (hormonal therapy and chemotherapy), and radiation.

Worldwide, breast cancer comprises 10.4% of all cancer incidence among women, making it the second most common type of non-skin cancer (after lung cancer) and the fifth most common cause of cancer death. In 2004, breast cancer caused 519,000 deaths worldwide (7% of cancer deaths; almost 1% of all deaths). Breast cancer is about 100 times more common in women than in men, although males tend to have poorer outcomes due to delays in diagnosis.

Some breast cancers require the hormones estrogen and progesterone to grow, and have receptors for those hormones. After surgery those cancers are treated with drugs that interfere with those hormones, usually tamoxifen, and with drugs that shut off the production of estrogen in the ovaries or elsewhere; this may damage the ovaries and end fertility. After surgery, low-risk, hormone-sensitive breast cancers may be treated with hormone therapy and radiation alone. Breast cancers without hormone receptors, or which have spread to the lymph nodes in the armpits, or which express certain genetic characteristics, are higher-risk, and are treated more aggressively. One standard regimen, popular in the U.S., is cyclophosphamide plus doxorubicin (Adriamycin), known as CA; these drugs damage DNA in the cancer, but also in fast-growing normal cells where they cause serious side effects. Sometimes a taxane drug, such as docetaxel, is added, and the regime is then known as CAT; taxane attacks the microtubules in cancer cells. An equivalent treatment, popular in Europe, is cyclophosphamide, methotrexate, and fluorouracil (CMF). Monoclonal antibodies, such as trastuzumab (Herceptin), are used for cancer cells that have the HER2 mutation. Radiation is usually added to the surgical bed to control cancer cells that were missed by the surgery, which usually extends survival, although radiation exposure to the heart may cause damage and heart failure in the following years.

While screening techniques (which are further discussed below) are useful in determining the possibility of cancer, a further testing is necessary to confirm whether a lump detected on screening is cancer, as opposed to a benign alternative such as a simple cyst.

In a clinical setting, breast cancer is commonly diagnosed using a "triple test" of clinical breast examination (breast examination by a trained medical practitioner), mammography, and fine needle aspiration cytology. Both mammography and clinical breast exam, also used for screening, can indicate an approximate likelihood that a lump is cancer, and may also identify any other lesions. Fine Needle Aspiration and Cytology (FNAC), which may be done in a doctor's office using local anaesthetic if required, involves attempting to extract a small portion of fluid from the lump. Clear fluid makes the lump highly unlikely to be cancerous, but bloody fluid may be sent off for inspection under a microscope for cancerous cells. Together, these three tools can be used to diagnose breast cancer with a good degree of accuracy. Other options for biopsy include core biopsy, where a section of the breast lump is removed, and an excisional biopsy, where the entire lump is removed.

In addition vacuum-assisted breast biopsy (VAB) may help diagnose breast cancer among patients with a mammographically detected breast in women according to a systematic review. In this study, summary estimates for vacuum assisted breast biopsy in diagnosis of breast cancer were as follows sensitivity was 98.1% with 95% CI=0.972-0.987 and specificity was 100% with 95% CI=0.997-0.999. However underestimate rates of atypical ductal hyperplasia (ADH) and ductal carcinoma in situ (DCIS) were 20.9% with 95% CI=0.177-0.245 and 11.2% with 95% CI=0.098-0.128 respectively.

Breast cancer screening refers to testing otherwisehealthy women for breast cancer in an attempt to achieve an earlier diagnosis. The assumption is that early detection will improve outcomes. A number of screening test have been employed including: clinical and self breast exams, mammography, genetic screening, ultrasound, and magnetic resonance imaging.

A clinical or self breast exam involves feeling the breast for lumps or other abnormalities. Research evidence does not support the effectiveness of either type of breast exam, because by the time a lump is large enough to be found it is likely to have been growing for several years and will soon be large enough to be found without an exam. Mammographic screening for breast cancer uses x-rays to examine the breast for any uncharacteristic masses or lumps. In women at high risk, such as those with a strong family history of cancer, mammography screening is recommended at an earlier age and additional testing may include genetic screening that tests for the BRCA genes and/or magnetic resonance imaging.

Breast cancer is sometimes treated first with surgery, and then with chemotherapy, radiation, or both. Treatments are given with increasing aggressiveness according to the prognosis and risk of recurrence. Stage 1 cancers (and DCIS) have an excellent prognosis and are generally treated with lumpectomy with or without chemotherapy or radiation. Although the aggressive HER2+ cancers should also be treated with the trastuzumab (Herceptin) regime. Stage 2 and 3 cancers with a progressively poorer prognosis and greater risk of recurrence are generally treated with surgery (lumpectomy or mastectomy with or without lymph node removal), radiation (sometimes) and chemotherapy (plus trastuzumab for HER2+ cancers). Stage 4, metastatic cancer, (i.e., spread to distant sites) is not curable and is managed by various combinations of all treatments from surgery, radiation, chemotherapy and targeted therapies. These treatments increase the median survival time of stage 4 breast cancer by about 6 months.

Breast cancer subtypes are typically categorized on an immunohistochemical basis. Subtype definitions are general as follows:
- normal (ER+, PR+, HER2+, cytokeratin 5/6+, and HER1+)
- luminal A (ER+ and/or PR+, HER2−)
- luminal B (ER+ and/or PR+, HER2+)
- triple-negative (ER−, PR−, HER2−)
- HER2+/ER− (ER−, PR−, and HER2+)
- unclassified (ER−, PR−, HER2−, cytokeratin 5/6−, and HER1−)

In the case of triple-negative breast cancer cells, the cancer's growth is not driven by estrogen or progesterone, or by growth signals coming from the HER2 protein. By the same token, such cancer cells do not respond to hormonal therapy, such as tamoxifen or aromatase inhibitors, or therapies that target HER2 receptors, such as Herceptin®. About 10-20% of breast cancers are found to be triple-negative. It is important to identify these types of cancer so that one can avoid costly and toxic effects of therapies that are unlike to succeed, and to focus on treatements that can be used to treat triple-negative breast cancer. Like other forms of breast cancer, triple-negative breast cancer can be treated with surgery, radiation therapy, and/or chemotherapy. One particularly promising approach is "neoadjuvant" therapy, where chemo- and/or radiotherapy is provided prior to surgery. Another drug therapy is the use of poly (ADP-ribose) polymerase, or PARP inhibitors.

2. Ovarian Cancer

Ovarian cancer is a cancerous growth arising from different parts of the ovary. Most (>90%) ovarian cancers are classified as "epithelial" and were believed to arise from the surface (epithelium) of the ovary. However, recent evidence suggests that the Fallopian tube could also be the source of some ovarian cancers. Since the ovaries and tubes are closely related to each other, it is hypothesized that these cells can mimic ovarian cancer. Other types arise from the egg cells (germ cell tumor) or supporting cells (sex cord/stromal).

In 2004, in the United States, 25,580 new cases were diagnosed and 16,090 women died of ovarian cancer. The risk increases with age and decreases with pregnancy. Lifetime risk is about 1.6%, but women with affected first-degree relatives have a 5% risk. Women with a mutated BRCA1 or BRCA2 gene carry a risk between 25% and 60% depending on the specific mutation. Ovarian cancer is the fifth leading cause of death from cancer in women and the leading cause of death from gynecological cancer.

Ovarian cancer causes non-specific symptoms. Early diagnosis would result in better survival, on the assumption that stage I and II cancers progress to stage III and IV cancers (but this has not been proven). Most women with ovarian cancer report one or more symptoms such as abdominal pain or discomfort, an abdominal mass, bloating, back pain, urinary urgency, constipation, tiredness and a range of other non-specific symptoms, as well as more specific symptoms such as pelvic pain, abnormal vaginal bleeding or involuntary weight loss. There can be a build-up of fluid (ascites) in the abdominal cavity.

Diagnosis of ovarian cancer starts with a physical examination (including a pelvic examination), a blood test (for CA-125 and sometimes other markers), and transvaginal ultrasound. The diagnosis must be confirmed with surgery to inspect the abdominal cavity, take biopsies (tissue samples for microscopic analysis) and look for cancer cells in the abdominal fluid. Treatment usually involves chemotherapy and surgery, and sometimes radiotherapy.

In most cases, the cause of ovarian cancer remains unknown. Older women, and in those who have a first or second degree relative with the disease, have an increased risk. Hereditary forms of ovarian cancer can be caused by mutations in specific genes (most notably BRCA1 and BRCA2, but also in genes for hereditary nonpolyposis colorectal cancer). Infertile women and those with a condition called endometriosis, those who have never been pregnant and those who use postmenopausal estrogen replacement therapy are at increased risk. Use of combined oral contraceptive pills is a protective factor. The risk is also lower in women who have had their uterine tubes blocked surgically (tubal ligation).

Ovarian cancer is classified according to the histology of the tumor, obtained in a pathology report. Histology dictates many aspects of clinical treatment, management, and prognosis. Surface epithelial-stromal tumour, also known as ovarian epithelial carcinoma, is the most common type of ovarian cancer. It includes scrous tumour, endometrioid tumor and mucinous cystadenocarcinoma. Sex cord-stromal tumor, including estrogen-producing granulosa cell tumor and virilizing Sertoli-Leydig cell tumor or arrhenoblastoma, accounts for 8% of ovarian cancers. Germ cell tumor accounts for approximately 30% of ovarian tumors but only 5% of ovarian cancers, because most germ cell tumors are teratomas and most teratomas are benign (see Teratoma). Germ cell tumor tends to occur in young women and girls. The prognosis depends on the specific histology of germ cell tumor, but overall is favorable. Mixed tumors, containing elements of more than one of the above classes of tumor histology.

Ovarian cancer can also be a secondary cancer, the result of metastasis from a primary cancer elsewhere in the body. Seven percent of ovarian cancers are due to metastases while the rest are primary cancers. Common primary cancers are breast cancer and gastrointestinal cancer (a common mistake is to name all peritoneal metastases from any gastrointestinal cancer as Krukenberg cancer, but this is only the case if it originates from primary gastric cancer). Surface epithelial-stromal tumor can originate in the peritoneum (the lining of the abdominal cavity), in which case the ovarian cancer is secondary to primary peritoneal cancer, but treatment is basically the same as for primary surface epithelial-stromal tumor involving the peritoneum.

Ovarian cancer staging is by the FIGO staging system and uses information obtained after surgery, which can include a total abdominal hysterectomy, removal of (usually) both ovaries and fallopian tubes, (usually) the omentum, and pelvic (peritoneal) washings for cytopathology. The AJCC stage is the same as the FIGO stage. The AJCC staging system describes the extent of the primary Tumor (T), the absence or presence of metastasis to nearby lymph Nodes (N), and the absence or presence of distant Metastasis (M).

The AJCC/TNM staging system includes three categories for ovarian cancer, T, N and M. The T category contains three other subcategories, T1, T2 and T3, each of them being classified according to the place where the tumor has developed (in one or both ovaries, inside or outside the ovary). The T1 category of ovarian cancer describes ovarian tumors that are confined to the ovaries, and which may affect one or both of them. The sub-subcategory T1a is used to stage cancer that is found in only one ovary, which has left the capsule intact and which cannot be found in the fluid taken from the pelvis. Cancer that has not affected the capsule, is confined to the inside of the ovaries and cannot be found in the fluid taken from the pelvis but has affected both ovaries is staged as T1b. T1c category describes a type of tumor that can affect one or both ovaries, and which has grown through the capsule of an ovary or it is present in the fluid taken from the pelvis. T2 is a more advanced stage of cancer. In this case, the tumor has grown in one or both ovaries and is spread to the uterus, fallopian tubes or other pelvic tissues. Stage T2a is used to describe a cancerous tumor that has spread to the uterus or the fallopian tubes (or both) but which is not present in the fluid taken from the pelvis. Stages T2b and T2c indicate cancer that metastasized to other pelvic tissues than the uterus and fallopian tubes and which cannot be seen in the fluid taken from the pelvis, respectively tumors that spread to any of the pelvic tissues (including uterus and fallopian tubes) but which can also be found in the fluid taken from the pelvis. T3 is the stage used to describe cancer that has spread to the peritoneum. This stage provides information on the size of the metastatic tumors (tumors that are located in other areas of the body, but are caused by ovarian cancer). These tumors can be very small, visible only under the microscope (T3a), visible but not larger than 2 centimeters (T3b) and bigger than 2 centimeters (T3c).

This staging system also uses N categories to describe cancers that have or not spread to nearby lymph nodes. There are only two N categories, N0 which indicates that the cancerous tumors have not affected the lymph nodes, and N1 which indicates the involvement of lymph nodes close to the tumor. The M categories in the AJCC/TNM staging system provide information on whether the ovarian cancer has metastasized to distant organs such as liver or lungs. M0 indicates that the cancer did not spread to distant organs and M1 category is used for cancer that has spread to other organs of the body. The AJCC/TNM staging system also contains a Tx and a Nx sub-category which indicates that the extent of the tumor cannot be described because of insufficient data, respectively the involvement of the lymph nodes cannot be described because of the same reason.

Ovarian cancer, as well as any other type of cancer, is also graded, apart from staged. The histologic grade of a tumor measures how abnormal or malignant its cells look under the microscope. There are four grades indicating the likelihood of the cancer to spread and the higher the grade, the more likely for this to occur. Grade 0 is used to describe non-invasive tumors. Grade 0 cancers are also referred to as borderline tumors. Grade 1 tumors have cells that are well differentiated (look very similar to the normal tissue) and are the ones with the best prognosis. Grade 2 tumors are also called moderately well differentiated and they are made up by cells that resemble the normal tissue. Grade 3 tumors have the worst prognosis and their cells are abnormal, referred to as poorly differentiated.

The signs and symptoms of ovarian cancer are most of the times absent, but when they exist they are nonspecific. In most cases, the symptoms persist for several months until the patient is diagnosed. A prospective case-control study of 1,709 women visiting primary care clinics found that the combination of bloating, increased abdominal size, and urinary symptoms was found in 43% of those with ovarian cancer but in only 8% of those presenting to primary care clinics.

The exact cause is usually unknown. The risk of developing ovarian cancer appears to be affected by several factors. The more children a woman has, the lower her risk of ovarian cancer. Early age at first pregnancy, older age of final pregnancy and the use of low dose hormonal contraception have also been shown to have a protective effect. Ovarian cancer is reduced in women after tubal ligation.

The relationship between use of oral contraceptives and ovarian cancer was shown in a summary of results of 45 case-control and prospective studies. Cumulatively these studies show a protective effect for ovarian cancers. Women who used oral contraceptives for 10 years had about a 60% reduction in risk of ovarian cancer. (risk ratio 0.42 with statistical significant confidence intervals given the large study size, not unexpected). This means that if 250 women took oral contraceptives for 10 years, 1 ovarian cancer would be prevented. This is by far the largest epidemiological study to date on this subject (45 studies, over 20,000 women with ovarian cancer and about 80,000 controls).

The link to the use of fertility medication, such as Clomiphene citrate, has been controversial. An analysis in 1991 raised the possibility that use of drugs may increase the risk of ovarian cancer. Several cohort studies and case-control studies have been conducted since then without demonstrating conclusive evidence for such a link. It will remain a complex topic to study as the infertile population differs in parity from the "normal" population.

There is good evidence that in some women genetic factors are important. Carriers of certain mutations of the BRCA1 or the BRCA2 gene are notably at risk. The BRCA1 and BRCA2 genes account for 5%-13% of ovarian cancers and certain populations (e.g., Ashkenazi Jewish women) are at a higher risk of both breast cancer and ovarian cancer, often at an earlier age than the general population. Patients with a personal history of breast cancer or a family history of breast and/or ovarian cancer, especially if diagnosed at a young age, may have an elevated risk.

A strong family history of uterine cancer, colon cancer, or other gastrointestinal cancers may indicate the presence of a syndrome known as hereditary nonpolyposis colorectal cancer (HNPCC, also known as Lynch syndrome), which confers a higher risk for developing ovarian cancer. Patients with strong genetic risk for ovarian cancer may consider the use of prophylactic, i.e., preventative, oophorectomy after completion of childbearing. Australia being member of International Cancer Genome Consortium is leading efforts to map ovarian cancer's complete genome.

Ovarian cancer at its early stages (I/II) is difficult to diagnose until it spreads and advances to later stages (III/IV). This is because most symptoms are non-specific and thus of little use in diagnosis. When an ovarian malignancy is included in the list of diagnostic possibilities, a limited number of laboratory tests are indicated. A complete blood count (CBC) and serum electrolyte test should be obtained in all patients. The serum BHCG level should be measured in any female in whom pregnancy is a possibility. In addition, serum α-fetoprotein (AFP) and lactate dehydrogenase (LDH) should be measured in young girls and adolescents with suspected ovarian tumors because the younger the patient, the greater the likelihood of a malignant germ cell tumor. A blood test called CA-125 is useful in differential diagnosis and in follow up of the disease, but it by itself has not been shown to be an effective method to screen for early-stage ovarian cancer due to its unacceptable low sensitivity and specificity. However, this is the only widely-used marker currently available.

Current research is looking at ways to combine tumor markers proteomics along with other indicators of disease (i.e., radiology and/or symptoms) to improve accuracy. The challenge in such an approach is that the very low population prevalence of ovarian cancer means that even testing with very high sensitivity and specificity will still lead to a number of false positive results (i.e., performing surgical procedures in which cancer is not found intra-operatively). However, the contributions of proteomics are still in the early stages and require further refining. Current studies on proteomics mark the beginning of a paradigm shift towards individually tailored therapy.

A pelvic examination and imaging including CT scan and trans-vaginal ultrasound are essential. Physical examination may reveal increased abdominal girth and/or ascites (fluid within the abdominal cavity). Pelvic examination may reveal an ovarian or abdominal mass. The pelvic examination can include a rectovaginal component for better palpation of the ovaries. For very young patients, magnetic resonance imaging may be preferred to rectal and vaginal examination.

To definitively diagnose ovarian cancer, a surgical procedure to take a look into the abdomen is required. This can be an open procedure (laparotomy, incision through the abdominal wall) or keyhole surgery (laparoscopy). During this procedure, suspicious areas will be removed and sent for microscopic analysis. Fluid from the abdominal cavity can also be analysed for cancerous cells. If there is cancer, this procedure can also determine its spread (which is a form of tumor staging).

Women who have had children are less likely to develop ovarian cancer than women who have not, and breastfeeding may also reduce the risk of certain types of ovarian cancer. Tubal ligation and hysterectomy reduce the risk and removal of both tubes and ovaries (bilateral salpingo-oophorectomy) dramatically reduces the risk of not only ovarian cancer but breast cancer also. The use of oral contraceptives (birth control pills) for five years or more decreases the risk of ovarian cancer in later life by 50%.

Tubal ligation is believed to decrease the chance of developing ovarian cancer by up to 67% while a hysterectomy may reduce the risk of getting ovarian cancer by about one-third. Moreover, according to some studies, analgesics such as acetaminophen and aspirin seem to reduce one's risks of developing ovarian cancer. Yet, the information is not consistent and more research needs to be carried on this matter.

Routine screening of women for ovarian cancer is not recommended by any professional society—this includes the U.S. Preventive Services Task Force, the American Cancer Society, the American College of Obstetricians and Gynecologists, and the National Comprehensive Cancer Network. This is because no trial has shown improved survival for women undergoing screening. Screening for any type of cancer must be accurate and reliable—it needs to accurately detect the disease and it must not give false positive results in people who do not have cancer. As yet there is no technique for ovarian screening that has been shown to fulfill these criteria. However in some countries such as the UK, women who are likely to have an increased risk of ovarian cancer (for example if they have a family history of the disease) can be offered individual screening through their doctors, although this will not necessarily detect the disease at an early stage.

Researchers are assessing different ways to screen for ovarian cancer. Screening tests that could potentially be used alone or in combination for routine screening include the CA-125 marker and transvaginal ultrasound. Doctors can measure the levels of the CA-125 protein in a woman's blood—high levels could be a sign of ovarian cancer, but this is not always the case. And not all women with ovarian cancer have high CA-125 levels. Transvaginal ultrasound involves using an ultrasound probe to scan the ovaries from inside the vagina, giving a clearer image than scanning the abdomen. The UK Collaborative Trial of Ovarian Cancer Screening is testing a screening technique that combines CA-125 blood tests with transvaginal ultrasound.

The purpose of screening is to diagnose ovarian cancer at an early stage, when it is more likely to be treated successfully. However, the development of the disease is not fully understood, and it has been argued that early-stage cancers may not always develop into late-stage disease. With any screening technique there are risks and benefits that need to be carefully considered, and health authorities need to assess these before introducing any ovarian cancer screening programs.

The goal of ovarian cancer screening is to detect the disease at stage I. Several large studies are ongoing, but none have identified an effective technique. In 2009, however, early results from the UK Collaborative Trial of Ovarian Cancer Screening (UKCTOCS) showed that a technique combining annual CA-125 tests with ultrasound imaging did help to detect the disease at an early stage. However, it is not yet clear if this approach could actually help to save lives—the full results of the trial will be published in 2015.

Surgical treatment may be sufficient for malignant tumors that are well-differentiated and confined to the ovary. Addition of chemotherapy may be required for more aggressive tumors that are confined to the ovary. For patients with advanced disease a combination of surgical reduction with a combination chemotherapy regimen is standard. Borderline tumors, even following spread outside of the ovary, are managed well with surgery, and chemotherapy is not seen as useful.

Surgery is the preferred treatment and is frequently necessary to obtain a tissue specimen for differential diagnosis via its histology. Surgery performed by a specialist in gynecologic oncology usually results in an improved result. Improved survival is attributed to more accurate staging of the disease and a higher rate of aggressive surgical excision of tumor in the abdomen by gynecologic oncologists as opposed to general gynecologists and general surgeons.

The type of surgery depends upon how widespread the cancer is when diagnosed (the cancer stage), as well as the presumed type and grade of cancer. The surgeon may remove one (unilateral oophorectomy) or both ovaries (bilateral oophorectomy), the fallopian tubes (salpingectomy), and the uterus (hysterectomy). For some very early tumors (stage 1, low grade or low-risk disease), only the involved ovary and fallopian tube will be removed (called a "unilateral salpingo-oophorectomy," USO), especially in young females who wish to preserve their fertility.

In advanced malignancy, where complete resection is not feasible, as much tumor as possible is removed (debulking surgery). In cases where this type of surgery is successful (i.e., <1 cm in diameter of tumor is left behind, "optimal debulking"), the prognosis is improved compared to patients where large tumor masses (>1 cm in diameter) are left behind. Minimally invasive surgical techniques may facilitate the safe removal of very large (greater than 10 cm) tumors with fewer complications of surgery.

Chemotherapy has been a general standard of care for ovarian cancer for decades, although with highly variable protocols. Chemotherapy is used after surgery to treat any residual disease, if appropriate. This depends on the histology of the tumor; some kinds of tumor (particularly teratoma) are not sensitive to chemotherapy. In some cases, there may be reason to perform chemotherapy first, followed by surgery. For patients with stage IIIC epithelial ovarian adenocarcinomas who have undergone successful optimal debulking, a recent clinical trial demonstrated that median survival time is significantly longer for patient receiving intraperitoneal (IP) chemotherapy. Patients in this clinical trial reported less compliance with IP chemotherapy and fewer than half of the patients received all six cycles of IP chemotherapy. Despite this high "drop-out" rate, the group as a whole (including the patients that didn't complete IP chemotherapy treatment) survived longer on average than patients who received intravenous chemotherapy alone.

Some specialists believe the toxicities and other complications of IP chemotherapy will be unnecessary with improved IV chemotherapy drugs currently being developed. Although IP chemotherapy has been recommended as a standard of care for the first-line treatment of ovarian cancer, the basis for this recommendation has been challenged.

Radiation therapy is not effective for advanced stages because when vital organs are in the radiation field, a high dose cannot be safely delivered. Radiation therapy is then commonly avoided in such stages as the vital organs may not be able to withstand the problems associated with these ovarian cancer treatments.

Ovarian cancer usually has a poor prognosis. It is disproportionately deadly because it lacks any clear early detection or screening test, meaning that most cases are not diagnosed until they have reached advanced stages. More than 60% of women presenting with this cancer already have stage III or stage IV cancer, when it has already spread beyond the ovaries. Ovarian cancers shed cells into the naturally occurring fluid within the abdominal cavity. These cells can then implant on other abdominal (peritoneal) structures, included the uterus, urinary bladder, bowel and the lining of the bowel wall omentum forming new tumor growths before cancer is even suspected. The five-year survival rate for all stages of ovarian cancer is 45.5%. For cases where a diagnosis is made early in the disease, when the cancer is still confined to the primary site, the five-year survival rate is 92.7%.

3. Gliomas

Glioblastoma multiforme is the deadliest and most common form of malignant brain tumor. Even when aggressive multimodality therapy consisting of radiotherapy, chemotherapy, and surgical excision is used, median survival is only 12-17 months. Standard therapy for glioblastoma multiforme consists of maximal surgical resection of the tumor, followed by radiotherapy between two and four weeks after the surgical procedure to remove the cancer. This is followed by chemotherapy. Most patients with glioblastoma take a corticosteroid, typically dexamethasone, during their illness to palliate symptoms. Experimental treatments include gamma-knife radiosurgery, boron neutron capture therapy and gene transfer.

Although there is no specific or singular clinical symptom or sign for any brain tumors, the presence of a combination of symptoms and the lack of corresponding clinical indications of infections or other causes can be an indicator to redirect diagnostic investigation towards the possibility of an intracranial neoplasm.

The diagnosis will often start with an interrogation of the patient to get a clear view of his medical antecedents, and his current symptoms. Clinical and laboratory investigations will serve to exclude infections as the cause of the symptoms. Examinations in this stage may include ophtamological, otolaryngological (or ENT) and/or electrophysiological exams. The use of electroencephalography (EEG) often plays a role in the diagnosis of brain tumors.

Swelling, or obstruction of the passage of cerebrospinal fluid (CSF) from the brain may cause (early) signs of increased intracranial pressure which translates clinically into headaches, vomiting, or an altered state of consciousness, and in children changes to the diameter of the skull and bulging of the fontanelles. More complex symptoms such as endocrine dysfunctions should alarm doctors not to exclude brain tumors.

A bilateral temporal visual field defect (due to compression of the optic chiasm) or dilatation of the pupil, and the occurrence of either slowly evolving or the sudden onset of focal neurologic symptoms, such as cognitive and behavioral impairment (including impaired judgment, memory loss, lack of recognition, spatial orientation disorders), personality or emotional changes, hemiparesis, hypoesthesia, aphasia, ataxia, visual field impairment, impaired sense of smell, impaired hearing, facial paralysis, double vision, or more severe symptoms such as tremors, paralysis on one side of the body hemiplegia, or (epileptic) seizures in a patient with a negative history for epilepsy, should raise the possibility of a brain tumor.

Imaging plays a central role in the diagnosis of brain tumors. Early imaging methods—invasive and sometimes dangerous—such as pneumoencephalography and cerebral angiography, have been abandoned in recent times in favor of non-invasive, high-resolution techniques, such as computed tomography (CT)-scans and especially magnetic resonance imaging (MRI). Neoplasms will often show as differently colored masses (also referred to as processes) in CT or MRI results.

Benign brain tumors often show up as hypodense (darker than brain tissue) mass lesions on cranial CT-scans. On MRI, they appear either hypo- (darker than brain tissue) or isointense (same intensity as brain tissue) on T1-weighted scans, or hyperintense (brighter than brain tissue) on T2-weighted MRI, although the appearance is variable.

Contrast agent uptake, sometimes in characteristic patterns, can be demonstrated on either CT or MRI-scans in most malignant primary and metastatic brain tumors. Perifocal edema, or pressure-areas, or where the brain tissue has been compressed by an invasive process also appears hyperintense on T2-weighted MRI might indicate the presence a diffuse neoplasm (unclear outline). This is because these tumors disrupt the normal functioning of the blood-brain barrier and lead to an increase in its permeability. However it is not possible to diagnose high versus low grade gliomas based on enhancement pattern alone.

Glioblastoma multiforme and anaplastic astrocytoma have been associated with the genetic acute hepatic porphyrias (PCT, AIP, HCP and VP), including positive testing associated with drug refractory seizures. Unexplained complications associated with drug treatments with these tumors should alert physicians to an undiagnosed neurological porphyria.

The definitive diagnosis of brain tumor can only be confirmed by histological examination of tumor tissue samples obtained either by means of brain biopsy or open surgery. The histological examination is essential for determining the appropriate treatment and the correct prognosis. This examination, performed by a pathologist, typically has three stages: interoperative examination of fresh tissue, preliminary microscopic examination of prepared tissues, and followup examination of prepared tissues after immunohistochemical staining or genetic analysis.

When a brain tumor is diagnosed, a medical team will be formed to assess the treatment options presented by the leading surgeon to the patient and his/her family. Given the location of primary solid neoplasms of the brain in most cases a "do-nothing" option is usually not presented. Neurosurgeons take the time to observe the evolution of the neoplasm before proposing a management plan to the patient and his/her relatives. These various types of treatment are available depending on neoplasm type and location and may be combined to give the best chances of survival: surgery: complete or partial resection of the tumor with the objective of removing as many tumor cells as possible; radiotherapy; and chemotherapy, with the aim of killing as many as possible of cancerous cells left behind after surgery and of putting remaining tumor cells into a nondividing, sleeping state for as long as possible.

Survival rates in primary brain tumors depend on the type of tumor, age, functional status of the patient, the extent of surgical tumor removal and other factors specific to each case.

The primary and most desired course of action described in medical literature is surgical removal (resection) via craniotomy. Minimally invasive techniques are being studied but are far from being common practice. The prime remediating objective of surgery is to remove as many tumor cells as possible, with complete removal being the best outcome and cytoreduction ("debulking") of the tumor otherwise. In some cases access to the tumor is impossible and impedes or prohibits surgery.

Several current research studies aim to improve the surgical removal of brain tumors by labeling tumor cells with a chemical (5-aminolevulinic acid) that causes them to fluoresce. Post-operative radiotherapy and chemotherapy are integral parts of the therapeutic standard for malignant tumors. Radiotherapy may also be administered in cases of "low-grade" gliomas, when a significant tumor burden reduction could not be achieved surgically.

Any person undergoing brain surgery may suffer from epileptic seizures. Seizures can vary from absences to severe tonic-clonic attacks. Medication is prescribed and administered to minimize or eliminate the occurrence of seizures.

Multiple metastatic tumors are generally treated with radiotherapy and chemotherapy rather than surgery. The prognosis in such cases is determined by the primary tumor, but is generally poor.

The goal of radiation therapy is to selectively kill tumor cells while leaving normal brain tissue unharmed. In standard external beam radiation therapy, multiple treatments of standard-dose "fractions" of radiation are applied to the brain. This process is repeated for a total of 10 to 30 treatments, depending on the type of tumor. This additional treatment provides some patients with improved outcomes and longer survival rates.

Radiosurgery is a treatment method that uses computerized calculations to focus radiation at the site of the tumor while minimizing the radiation dose to the surrounding brain. Radiosurgery may be an adjunct to other treatments, or it may represent the primary treatment technique for some tumors.

Radiotherapy may be used following, or in some cases in place of, resection of the tumor. Forms of radiotherapy used for brain cancer include external beam radiation therapy, brachytherapy, and in more difficult cases, stereotactic radiosurgery, such as Gamma knife, Cyberknife or Novalis Tx radiosurgery.

Radiotherapy is the most common treatment for secondary brain tumors. The amount of radiotherapy depends on the size of the area of the brain affected by cancer. Conventional external beam 'whole brain radiotherapy treatment' (WBRT) or 'whole brain irradiation' may be suggested if there is a risk that other secondary tumors will develop in the future. Stereotactic radiotherapy is usually recommended in cases involving fewer than three small secondary brain tumors.

Patients undergoing chemotherapy are administered drugs designed to kill tumor cells. Although chemotherapy may improve overall survival in patients with the most malignant primary brain tumors, it does so in only about 20 percent of patients. Chemotherapy is often used in young children instead of radiation, as radiation may have negative effects on the developing brain. The decision to prescribe this treatment is based on a patient's overall health, type of tumor, and extent of the cancer. The toxicity and many side effects of the drugs, and the uncertain outcome of chemotherapy in brain tumors puts this treatment further down the line of treatment options with surgery and radiation therapy preferred.

A shunt is used not as a cure but to relieve symptoms by reducing hydrocephalus caused by blockage of cerebrospinal fluid.

Researchers are presently investigating a number of promising new treatments including gene therapy, highly focused radiation therapy, immunotherapy and novel chemotherapies. A variety of new treatments are being made available on an investigational basis at centers specializing in brain tumor therapies.

4. Prostate Cancer

Prostate cancer is a disease in which cancer develops in the prostate, a gland in the male reproductive system. In 2007, almost 220,000 new cases were reported, and over 27,000 deaths were attributed to this malignancy. It occurs when cells of the prostate mutate and begin to multiply out of control. These cells may spread (metastasize) from the prostate to other parts of the body, especially the bones and lymph nodes. Prostate cancer may cause pain, difficulty in urinating, erectile dysfunction and other symptoms.

Rates of prostate cancer vary widely across the world. Although the rates vary widely between countries, it is least common in South and East Asia, more common in Europe, and most common in the United States. According to the American Cancer Society, prostate cancer is least common among Asian men and most common among black men, with figures for white men in-between. However, these high rates may be affected by increasing rates of detection.

Prostate cancer develops most frequently in men over fifty. This cancer can occur only in men, as the prostate is exclusively of the male reproductive tract. It is the most common type of cancer in men in the United States, where it is responsible for more male deaths than any other cancer, except lung cancer. However, many men who develop prostate cancer never have symptoms, undergo no therapy, and eventually die of other causes. Many factors, including genetics and diet, have been implicated in the development of prostate cancer.

Prostate cancer screening is an attempt to find unsuspected cancers. Screening tests may lead to more specific follow-up tests such as a biopsy, where small pieces of the prostate are removed for closer study. As of 2006 prostate cancer screening options include the digital rectal exam and the prostate specific antigen (PSA) blood test. Screening for prostate cancer is controversial because it is not clear if the benefits of screening outweigh the risks of follow-up diagnostic tests and cancer treatments.

Prostate cancer is a slow-growing cancer, very common among older men. In fact, most prostate cancers never grow to the point where they cause symptoms, and most men with prostate cancer die of other causes before prostate cancer has an impact on their lives. The PSA screening test may detect these small cancers that would never become life threatening. Doing the PSA test in these men may lead to overdiagnosis, including additional testing and treatment. Follow-up tests, such as prostate biopsy, may cause pain, bleeding and infection. Prostate cancer treatments may cause urinary incontinence and erectile dysfunction. Therefore, it is essential that the risks and benefits of diagnostic procedures and treatment be carefully considered before PSA screening.

Prostate cancer screening generally begins after age 50, but this can vary due to ethnic backgrounds. Thus, the American Academy of Family Physicians and American College of Physicians recommend the physician discuss the risks and benefits of screening and decide based on individual patient preference. Although there is no officially recommended cutoff, many health care providers stop monitoring PSA in men who are older than 75 years old because of concern that prostate cancer therapy may do more harm than good as age progresses and life expectancy decreases.

Digital rectal examination (DRE) is a procedure where the examiner inserts a gloved, lubricated finger into the rectum to check the size, shape, and texture of the prostate. Areas which are irregular, hard or lumpy need further evaluation, since they may contain cancer. Although the DRE only evaluates the back of the prostate, 85% of prostate cancers arise in this part of the prostate. Prostate cancer which can be felt on DRE is generally more advanced. The use of DRE has never been shown to prevent prostate cancer deaths when used as the only screening test.

The PSA test measures the blood level of prostate-specific antigen, an enzyme produced by the prostate. Specifically, PSA is a serine protease similar to kallikrein. Its normal function is to liquify gelatinous semen after ejaculation, allowing spermatazoa to more easily navigate through the uterine cervix.

PSA levels under 4 ng/mL are generally considered normal, however in individuals below the age of 50 sometimes a cutoff of 2.5 is used for the upper limit of normal, while levels over 4 ng/mL are considered abnormal (although in men over 65 levels up to 6.5 ng/mL may be acceptable, depending upon each laboratory's reference ranges). PSA levels between 4 and 10 ng/mL indicate a risk of prostate cancer higher than normal, but the risk does not seem to rise within this six-point range. When the PSA level is above 10 ng/mL, the association with cancer becomes stronger. However, PSA is not a perfect test. Some men with prostate cancer do not have an elevated PSA, and most men with an elevated PSA do not have prostate cancer.

PSA levels can change for many reasons other than cancer. Two common causes of high PSA levels are enlargement of the prostate (benign prostatic hypertrophy (BPH)) and infection in the prostate (prostatitis). It can also be raised for 24 hours after ejaculation and several days after catheterization. PSA levels are lowered in men who use medications used to treat BPH or baldness. These medications, finasteride (marketed as Proscar or Propecia) and dutasteride (marketed as Avodart), may decrease the PSA levels by 50% or more.

Several other ways of evaluating the PSA have been developed to avoid the shortcomings of simple PSA screening. The use of age-specific reference ranges improves the sensitivity and specificity of the test. The rate of rise of the PSA over time, called the PSA velocity, has been used to evaluate men with PSA levels between 4 and 10 ng/ml, but as of 2006, it has not proven to be an effective screening test. Comparing the PSA level with the size of the prostate, as measured by ultrasound or magnetic resonance imaging, has also been studied. This comparison, called PSA density, is both costly and, as of 2006, has not proven to be an effective screening test. PSA in the blood may either be free or bound to other proteins. Measuring the amount of PSA which is free or bound may provide additional screening information, but as of 2006, questions regarding the usefulness of these measurements limit their widespread use.

When a man has symptoms of prostate cancer, or a screening test indicates an increased risk for cancer, more invasive evaluation is offered. The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

If cancer is suspected, a biopsy is offered. During a biopsy a urologist obtains tissue samples from the prostate via the rectum. A biopsy gun inserts and removes special hollow-core needles (usually three to six on each side of the prostate) in less than a second. Prostate biopsies are routinely done on an outpatient basis and rarely require hospitalization. Fifty-five percent of men report discomfort during prostate biopsy.

The tissue samples are then examined under a microscope to determine whether cancer cells are present, and to evaluate the microscopic features of any cancer found. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate. In the TNM system, clinical T1 and T2 cancers are found only in the prostate, while T3 and T4 cancers have spread elsewhere. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans should reveal osteoblastic appearance due to increased bone density in the areas of bone metastisis—opposite to what is found in many other cancers that metastisize.

Prostate cancer can be treated with surgery, radiation therapy, hormonal therapy, occasionally chemotherapy, proton therapy, or some combination of these. The age and underlying health of the man as well as the extent of spread, appearance under the microscope, and response of the cancer to initial treatment are important in determining the outcome of the disease. Since prostate cancer is a disease of older men, many will die of other causes before a slowly advancing prostate cancer can spread or cause symptoms. This makes treatment selection difficult. The decision whether or not to treat localized prostate cancer (a tumor that is contained within the prostate) with curative intent is a patient trade-off between the expected beneficial and harmful effects in terms of patient survival and quality of life.

Watchful waiting, also called "active surveillance," refers to observation and regular monitoring without invasive treatment. Watchful waiting is often used when an early stage, slow-growing prostate cancer is found in an older man. Watchful waiting may also be suggested when the risks of surgery, radiation therapy, or hormonal therapy outweigh the possible benefits. Other treatments can be started if symptoms develop, or if there are signs that the cancer growth is accelerating (e.g., rapidly rising PSA, increase in Gleason score on repeat biopsy, etc.). Most men who choose watchful waiting for early stage tumors eventually have signs of tumor progression, and they may need to begin treatment within three years. Although men who choose watchful waiting avoid the risks of surgery and radiation, the risk of metastasis (spread of the cancer) may be increased. For younger men, a trial of active surveillance may not mean avoiding treatment altogether, but may reasonably allow a delay of a few years or more, during which time the quality of life impact of active treatment can be avoided. Published data to date suggest that carefully selected men will not miss a window for cure with this approach. Additional health problems that develop with advancing age during the observation period can also make it harder to undergo surgery and radiation therapy.

Clinically insignificant prostate tumors are often found by accident when a doctor incorrectly orders a biopsy not following the recommended guidelines (abnormal DRE and elevated PSA). The urologist must check that the PSA is not elevated for other reasons, prostatitis, etc. An annual biopsy is often recommended by a urologist for a patient who has selected watchful waiting when the tumor is clinically insignificant (no abnormal DRE or PSA). The tumors tiny size can be monitored this way and the patient can decide to have surgery only if the tumor enlarges which may take many years or never.

Surgical removal of the prostate, or prostatectomy, is a common treatment either for early stage prostate cancer, or for cancer which has failed to respond to radiation therapy. The most common type is radical retropubic prostatectomy, when the surgeon removes the prostate through an abdominal incision. Another type is radical perineal prostatectomy, when the surgeon removes the prostate through an incision in the perineum, the skin between the scrotum and anus. Radical prostatectomy can also be performed laparoscopically, through a series of small (1 cm) incisions in the abdomen, with or without the assistance of a surgical robot.

Radical prostatectomy is effective for tumors which have not spread beyond the prostate; cure rates depend on risk factors such as PSA level and Gleason grade. However, it may cause nerve damage that significantly alters the quality of life of the prostate cancer survivor. The most common serious complications are loss of urinary control and impotence. Reported rates of both complications vary widely depending on how they are assessed, by whom, and how long after surgery, as well as the setting (e.g., academic series vs. community-based or population-based data). Although penile sensation and the ability to achieve orgasm usually remain intact, erection and ejaculation are often impaired. Medications such as sildenafil (Viagra), tadalafil (Cialis), or vardenafil (Levitra) may restore some degree of potency. For most men with organ-confined disease, a more limited "nerve-sparing" technique may help avoid urinary incontinence and impotence.

Radical prostatectomy has traditionally been used alone when the cancer is small. In the event of positive margins or locally advanced disease found on pathology, adjuvant radiation therapy may offer improved survival. Surgery may also be offered when a cancer is not responding to radiation therapy. However, because radiation therapy causes tissue changes, prostatectomy after radiation has a higher risk of complications.

Transurethral resection of the prostate, commonly called a "TURP," is a surgical procedure performed when the tube from the bladder to the penis (urethra) is blocked by prostate enlargement. TURP is generally for benign disease and is not meant as definitive treatment for prostate cancer. During a TURP, a small tube (cystoscope) is placed into the penis and the blocking prostate is cut away.

In metastatic disease, where cancer has spread beyond the prostate, removal of the testicles (called orchiectomy) may be done to decrease testosterone levels and control cancer growth.

Radiation therapy, also known as radiotherapy, uses ionizing radiation to kill prostate cancer cells. When absorbed in tissue, ionizing radiation such as γ and x-rays damage the DNA in cells, which increases the probability of apoptosis. Two different kinds of radiation therapy are used in prostate cancer treatment: external beam radiation therapy and brachytherapy.

External beam radiation therapy uses a linear accelerator to produce high-energy x-rays which are directed in a beam towards the prostate. A technique called Intensity Modulated Radiation Therapy (IMRT) may be used to adjust the radiation beam to conform with the shape of the tumor, allowing higher doses to be given to the prostate and seminal vesicles with less damage to the bladder and rectum. External beam radiation therapy is generally given over several weeks, with daily visits to a radiation therapy center. New types of radiation therapy may have fewer side effects then traditional treatment, one of these is Tomotherapy.

Permanent implant brachytherapy is a popular treatment choice for patients with low to intermediate risk features, can be performed on an outpatient basis, and is associated with good 10-year outcomes with relatively low morbidity. It involves the placement of about 100 small "seeds" containing radioactive material (such as iodine$^{125}$ or palladium$^{103}$) with a needle through the skin of the perineum directly into the tumor while under spinal or general anesthetic. These seeds emit lower-energy X-rays which are only able to travel a short distance. Although the seeds eventually become inert, they remain in the prostate permanently. The risk of exposure to others from men with implanted seeds is generally accepted to be insignificant.

Radiation therapy is commonly used in prostate cancer treatment. It may be used instead of surgery for early cancers, and it may also be used in advanced stages of prostate cancer to treat painful bone metastases. Radiation treatments also can be combined with hormonal therapy for intermediate risk disease, when radiation therapy alone is less likely to cure the cancer. Some radiation oncologists combine external beam radiation and brachytherapy for intermediate to high risk situations. One study found that the combination of six months of androgen suppressive therapy combined with external beam radiation had improved survival compared to radiation alone in patients with localized prostate cancer. Others use a "triple modality" combination of external beam radiation therapy, brachytherapy, and hormonal therapy.

Less common applications for radiotherapy are when cancer is compressing the spinal cord, or sometimes after surgery, such as when cancer is found in the seminal vesicles, in the lymph nodes, outside the prostate capsule, or at the margins of the biopsy.

Radiation therapy is often offered to men whose medical problems make surgery more risky. Radiation therapy appears to cure small tumors that are confined to the prostate just about as well as surgery. However, as of 2006 some issues remain unresolved, such as whether radiation should be given to the rest of the pelvis, how much the absorbed dose should be, and whether hormonal therapy should be given at the same time.

Side effects of radiation therapy might occur after a few weeks into treatment. Both types of radiation therapy may cause diarrhea and rectal bleeding due to radiation proctitis, as well as urinary incontinence and impotence. Symptoms tend to improve over time. Men who have undergone external beam radiation therapy will have a higher risk of later developing colon cancer and bladder cancer.

Cryosurgery is another method of treating prostate cancer. It is less invasive than radical prostatectomy, and general anesthesia is less commonly used. Under ultrasound guidance, metal rods are inserted through the skin of the perineum into the prostate. Highly purified Argon gas is used to cool the rods, freezing the surrounding tissue at −196° C. (−320° F.). As the water within the prostate cells freeze, the cells die. The urethra is protected from freezing by a catheter filled with warm liquid. Cryosurgery generally causes fewer problems with urinary control than other treatments, but impotence occurs up to ninety percent of the time. When used as the initial treatment for prostate cancer and in the hands of an experienced cryosurgeon, cryosurgery has a 10 year biochemical disease free rate superior to all other treatments including radical prostatectomy and any form of radiation Cryosurgery has also been demonstrated to be superior to radical prostatectomy for recurrent cancer following radiation therapy.

Hormonal therapy uses medications or surgery to block prostate cancer cells from getting dihydrotestosterone (DHT), a hormone produced in the prostate and required for the growth and spread of most prostate cancer cells. Blocking DHT often causes prostate cancer to stop growing and even shrink. However, hormonal therapy rarely cures prostate cancer because cancers which initially respond to hormonal therapy typically become resistant after one to two years. Hormonal therapy is therefore usually used when cancer has spread from the prostate. It may also be given to certain men undergoing radiation therapy or surgery to help prevent return of their cancer.

Hormonal therapy for prostate cancer targets the pathways the body uses to produce DHT. A feedback loop involving the testicles, the hypothalamus, and the pituitary, adrenal, and prostate glands controls the blood levels of DHT. First, low blood levels of DHT stimulate the hypothalamus to produce gonadotropin releasing hormone (GnRH). GnRH then stimulates the pituitary gland to produce luteinizing hormone (LH), and LH stimulates the testicles to produce testosterone. Finally, testosterone from the testicles and dehydroepiandrosterone from the adrenal glands stimulate the prostate to produce more DHT. Hormonal therapy can decrease levels of DHT by interrupting this pathway at any point.

There are several forms of hormonal therapy. Orchiectomy is surgery to remove the testicles. Because the testicles make most of the body's testosterone, after orchiectomy testosterone levels drop. Now the prostate not only lacks the testosterone stimulus to produce DHT, but also it does not have enough testosterone to transform into DHT.

Anti-androgens are medications such as flutamide, bicalutamide, nilutamide, and cyproterone acetate which directly block the actions of testosterone and DHT within prostate cancer cells.

Medications which block the production of adrenal androgens such as DHEA include ketoconazole and aminoglutethimide. Because the adrenal glands only make about 5% of the body's androgens, these medications are generally used only in combination with other methods that can block the 95% of androgens made by the testicles. These combined methods are called total androgen blockade (TAB). TAB can also be achieved using antiandrogens.

GnRH action can be interrupted in one of two ways. GnRH antagonists suppress the production of LH directly, while GnRH agonists suppress LH through the process of downregulation after an initial stimulation effect. Abarelix is an example of a GnRH antagonist, while the GnRH agonists include leuprolide, goserelin, triptorelin, and buserelin. Initially, GnRH agonists increase the production of LH. However, because the constant supply of the medication does not match the body's natural production rhythm, production of both LH and GnRH decreases after a few weeks.

As of 2006 the most successful hormonal treatments are orchiectomy and GnRH agonists. Despite their higher cost, GnRH agonists are often chosen over orchiectomy for cosmetic and emotional reasons. Eventually, total androgen blockade may prove to be better than orchiectomy or GnRH agonists used alone.

Each treatment has disadvantages which limit its use in certain circumstances. Although orchiectomy is a low-risk surgery, the psychological impact of removing the testicles can be significant. The loss of testosterone also causes hot flashes, weight gain, loss of libido, enlargement of the breasts (gynecomastia), impotence and osteoporosis. GnRH agonists eventually cause the same side effects as orchiectomy but may cause worse symptoms at the beginning of treatment. When GnRH agonists are first used, testosterone surges can lead to increased bone pain from metastatic cancer, so antiandrogens or abarelix are often added to blunt these side effects. Estrogens are not commonly used because they increase the risk for cardiovascular disease and blood clots. The antiandrogens do not generally cause impotence and usually cause less loss of bone and muscle mass. Ketoconazole can cause liver damage with prolonged use, and aminoglutethimide can cause skin rashes.

Palliative care for advanced stage prostate cancer focuses on extending life and relieving the symptoms of metastatic disease. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone-refractory metastatic prostate cancer.

Bone pain due to metastatic disease is treated with opioid pain relievers such as morphine and oxycodone. External beam radiation therapy directed at bone metastases may provide pain relief Injections of certain radioisotopes, such as strontium$^{89}$, phosphorus$^{32}$, or samarium$^{153}$, also target bone metastases and may help relieve pain.

High Intensity Focused Ultrasound (HIFU) for prostate cancer utilizes ultrasonic waves to ablate/destroy the tissue of the prostate. During the HIFU procedure, sound waves are used to heat the prostate tissue thus destroying the cancerous cells. Essentially, ultrasonic waves are precisely focused on specific areas of the prostate to eliminate the prostate cancer with minimal risks of effecting other tissue or organs. Temperatures at the focal point of the sound waves can exceed 100° C. The ability to focus the ultrasonic waves leads to a relatively low occurrence of both incontinence and impotence. (0.6% and 0-20%, respectively). According to international studies, when compared to other procedures, HIFU has a high success rate with a reduced risk of side effects. Studies using the Sonablate 500 HIFU machine have shown that 94% of patients with a pretreatment PSA (Prostate Specific Antigen) of less than 10 g/ml were cancer-free after three years. However, many studies of HIFU were performed by manufacturers of HIFU devices, or members of manufacturers' advisory panels.

HIFU was first used in the 1940's and 1950's in efforts to destroy tumors in the central nervous system. Since then, HIFU has been shown to be effective at destroying malignant tissue in the brain, prostate, spleen, liver, kidney, breast, and bone. Today, the HIFU procedure for prostate cancer is performed using a transrectal probe. This procedure has been performed for over ten years and is currently approved for use in Japan, Europe, Canada, and parts of Central and South America.

Although not yet approved for use in the Unites States, many patients have received the HIFU procedure at facilities in Canada, and Central and South America. Currently, therapy is available using the Sonablate 500 or the Ablatherm. The Sonablate 500 is designed by Focus Surgery of Indianapolis, Ind. and is used in international HIFU centers around the world.

C. Combination Therapies

It is very common in the field of cancer therapy to combine therapeutic modalities. The following is a general discussion of therapies that may be used in conjunction with the therapies of the present disclosure.

To treat cancers using the methods and compositions of the present invention, one would generally contact a tumor cell or subject with a peptide and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the peptide and the other includes the other agent.

Alternatively, the peptide may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the peptide or the other therapy will be desired. Various combinations may be employed, where the peptide is "A," and the other therapy is "B," as exemplified below:

| | | | | |
|---|---|---|---|---|
| A/B/A | B/A/B | B/B/A | A/A/B | B/A/A |
| A/B/B | B/B/B/A | B/B/A/B | A/A/B/B | A/B/A/B |
| A/B/B/A | B/B/A/A | B/A/B/A | B/A/A/B | B/B/B/A |
| A/A/A/B | B/A/A/A | A/B/A/A | A/A/B/A | A/B/B/B |
| B/A/B/B | B/B/A/B | | | |

Other combinations are contemplated. The following is a general discussion of cancer therapies that may be used in combination with the peptides of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance antitumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used with the present invention. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

It also should be pointed out that any of the foregoing therapies may prove useful by themselves in treating cancer.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Model Cells.

Human Breast cancer cells MCF7, ZR75, and the ovarian cancer cell line BG1 were obtained from the American Type Culture Collection (ATCC) and were maintained using ATCC recommended media. Overexpression and stable knockdown of PELP1 in MCF7 and ZR75 models cells have been described previously (Nair et al., 2010a). Tamoxifen therapy resistant MCF7-TamR and letrozole resistant MCF7-LTLT cells were cultured in tamoxifen or letrozole ($10^{-7}$M) containing media in the presence or absence of peptides.

Cellular Lysates, Western Blot and Immunoprecipitation.

Cell lysates for western blot and immunoprecipitation were prepared as described previously (Nair et al., 2010b).

Yeast Two Hybrid Screen.

The Matchmaker GAL4 two-hybrid system 3 (Clontech) was performed according to manufacturer's protocol along with the Matchmaker random peptide library that contains 1E7 independent random peptide clones. PELP1 domains 1-400, 400-600, 600-866 and 960-1130 were cloned into the pGBKT7 vector that contains a GAL4 DNA-binding domain with BamH1 and XHO1 restriction sites. The peptides were clones into the pGADGH vector that contains the GAL4 activation domain with BamH1 and EcoR1 restriction sites. Positive clones were screened by GAL4 activation from PELP1-binding domain and peptide-activation domain interact and allow yeast to grow on plates lacking Histidine and Adenine. Minipreps (Promega) were used to isolate DNA from positive yeast clones identified by antibiotic selection which was transformed into E. coli and sequenced at the UTHSCSA genomics core.

Cellular Uptake Assay.

Peptides were conjugated with FITC with SureLINK Flouroscein Labeling Kit (KPL) as per manufacturing protocols. ZR75 cells were plated on coverslips in a 6 well plate with 100,000 cells/well in 8% RPMI and treated with FITC-labeled peptide for 30, 60 and 120 minutes. Cells were fixed with 3.7% paraformaldehyde, immunostained for PELP1 and nuclear staining with DAPI. Images were taken by confocal microscopy.

Cell Proliferation Assays.

Cell proliferation rates were measured by using MTT Cell Viability Assay in 96-well plates. Model cells were seeded in 96-well plates ($1 \times 10^3$ cells/well) in DMEM or RPMI medium containing 10% serum. After an overnight incubation, cells were treated with varying concentrations of the peptides for 3-7 days and growth inhibition was determined by using traditional MTT assay (Sigma) following manufacturer's instructions.

Migration Assays.

Models cells ZR75 and ZR75-PELP1 were cultured in steroid free medium for two days, treated with E2 (10-8M) in the presence or absence of PIPs (500 nM) and cell migration potential was analyzed using a Boyden chamber assay (Promega) as per manufacturer instructions.

TUNEL Assay.

ZR75 and ZR75PELP1 cells were plated on coverslips in 8% RPMI and treated with peptide for 24 hours. Cells were labeled with in situ Cell Death Detection Kit (Roche) according to manufacturer's protocol, imaged by fluorescent microscopy and quantified.

Therapy Resistance Assays:

Tamoxifen (Tam) therapy resistant MCF7-TamR and letrozole resistant MCF7-LTLT cells were cultured in tamoxifen or letrozole (10-7M) containing media in the presence or absence of peptides and proliferation was measured by MTT assay (Sigma) following manufacturer's instructions.

Reporter Gene Assays.

Model cells were seeded in 6-well plates. After overnight incubation, the cells were transfected with ERE-Luc plasmids using fugene for 6 h. Then, 24 hours after transfection, cells were incubated in 5% DCC media for estrogen starvation and then treated with TAT or PIP1/PIP2 for an additional 24 hours and estradiol ($10^{-8}$) for 12 hours. Each transfection was carried out in triplicate and normalized with the β-gal activity and total protein concentration. Luciferase activity was measured by using the luciferase assay system (Promega, Madison, Wis.).

Binding Assays.

Peptides were linked to EZ-Link NHS-Biotin (Thermo Scientific) per manutfacturer's protocol. TAT-biotin, PIP1-biotin or PIP2-bioting were bound to avidin beads were incubated for 1 hr at 4° C. at rotation with purified bacterial, full-length PELP1 in the presence of estrogen (E2) or nuclear lysates obtained from ZR75 cells treated with estradiol $10^{-8}$ M (Wysocka, 2006). Beads were washed 3× with IP buffer (20 mM HEPES pH 7.9, 20% glycerol, 0.1% triton-x, 100 mM KCl), eluted with SDS-dye, and PELP1 expression was determined by western blotting. GST binding assays were performed as described previously with recombinant G9a (NEB) (Nair et al., 2010b).

Mammosphere Assay.

ZR75PELP1 and MCF7PELP1 cells were FACS sorted for CD44-APC$^{high}$ (Milteny Biotec) and CD24-PE$^{low}$ (Milteny Biotec) cell surface markers. A single cell suspension of model cells ZR75-PELP1 were seeded in mammosphere media in a low adherent 96-well plate with TAT or PIP (10, 20 or 50 μM). Media containing peptide was added on day 4 and mammospheres were counted and imaged on day 8 (Shaw et al., 2012).

Soft Agar Colony Formation Assay.

Model cells MCF7, MCF7-PELP1, ZR75 and ZR75-PELP1 were seeded in a 0.6% agar solution with RPMI/10% FBS over a base agar layer in 35 mm plates in triplicate with TAT, PIP1, or PIP2 (10 μM). Media with peptide was added every 3 days and colonies were counted after 14 days.

Real Time PCR.

Model cells ZR75 and ZRPELP1KD were grown in 8% DCC media for 72 hours and treated with TAT or PIP1 (10 μM) for 12 hours. RNA was isolated by Trizol and cDNA was synthesized by Superscript III First Strand reverse transcriptase (Invitrogen). qPCR was performed in triplicate by SyberGreen using an Illumina Eco Real-Time PCR System. Gene expression was normalized to actin. The primer sequences are given below:

| | |
|---|---|
| PECAM1-Forward: | AACAGTGTTGACATGAAGAGCC (SEQ ID NO: 49) |
| PECAM1-Reverse: | TGTAAAACAGCACGTCATCCTT (SEQ ID NO: 50) |
| BMI1-Forward: | CCACCTGATGTGTGTGCTTTG (SEQ ID NO: 51) |
| BMI1-Reverse: | TTCAGTAGTGGTCTGGTCTTGT (SEQ ID NO: 52) |
| RB1-Forward: | CTCTCGTCAGGCTTGAGTTTG (SEQ ID NO: 53) |
| RB1-Reverse: | GACATCTCATCTAGGTCAACTGC (SEQ ID NO: 54) |
| SERAC1-Forward: | ATGTCCCTGGCTGCTTATTGC (SEQ ID NO: 55) |
| SERAC1-Reverse: | CCAGTGTGTGCCACTTTTTGG (SEQ ID NO: 56) |

Histone Methyltransferase Assay.

Recombinant Histone H3 was incubated with S-adenosyl methionine, purified bacterial PELP1 and recombinant purified G9a with TAT or PIP1 in histone methyltransferase buffer for 1 hour at 30° C. The reaction buffer contained ERα, estradiol $10^{-7}$ M, 50 mM Tris pH 8.0, 5 mM MgCl$_2$, and 4 mM DTT. The reaction was stopped by the addition of SDS dye and samples were run on a 15% SDS-PAGE gel and probed for H3K9me2 with Total H3 as the loading control.

ChIP sequencing.

ZR75 and ZR75PELP1 cells were grown in 5% DCC media for 72 hours and treated with estradiol ($10^{-8}$ M) for 30 minutes. Chromatin immunoprecipitation (ChIP) analysis was performed as described previously with H3K9me2 antibody (Upstate, 07-441) with IgG as control (Nair et al., 2004). ChIP was validated by qRTPCR of GREB1C: forward: TTGTTGTAGCTCTGGGAGCA (SEQ ID NO: 57), reverse: CAACCAGCCAAGAGGCTAAG (SEQ ID NO: 58). DNA library was prepared according to Illumina, and TruSeq DNA sample preparation and samples were run on Illumina HiSeq2000 in duplicate at the UTHSCA next generation sequencing core. The combined raw reads were aligned to UCSC hg19 and peaks were called by MACS analysis.

Synthesis of Peptides.

To enhance the cell permeability of the peptides, an additional TAT sequence was linked before the peptide sequence and synthesized by GenScript. The TAT sequence is GRKKRRQRRRGG (SEQ ID NO: 59).

```
                                    (SEQ ID NO: 59)
TAT:   GRKKRRQRRRGG (SEQ ID NO: 60)
PIP1:  GRKKRRQRRRGGMVEFRWSCPGRRKAKA (SEQ ID NO: 61)
PIP2:  GRKKRRQRRRGGIMGRGLCMRGVVRGRGRN (SEQ ID NO: 62)
PIP3:  GRKKRRQRRRGGFKEWWRIDMVWLHRVRRNSY
```

To enhance the half-life and efficacy of the peptide, the inventors employed "stapled peptide" technology. This technology uses stapling of the peptide at the α-helical structure which promotes cell penetration, enhances half-life, increases proteolytic resistance and enhances substrate specificity. The inventors have designed four possible stapled PIPs peptide (sPIP1-a, sPIP1-b, sPIP3-a, sPIP-3a) by incorporating special amino acids at i, i+4 position of the loop.

```
sPIP1-a:
Ac-MVEFR-S5-SCP-S5-RRKAKA-NH2
(Ac-SEQ ID NO: 63-S5-SCP-S5-SEQ ID NO: 64-NH2)

sPIP1-b:
Ac-MVE-S5-RWS-S5-PGRRKAKA-NH2
(Ac-MVE-S5-RWS-S5-SEQ ID NO: 65-NH2)

sPIP3-a:
Ac-FKEWWRI-S5-MVW-S5-HRVRRNSY-NH2
(Ac-SEQ ID NO: 66-S5-MVW-S5-SEQ ID NO: 67-NH2)

sPIP3-b:
Ac-FKEWWRIDMV-S5-LHR-S5-RRNSY-NH2
(Ac-SEQ ID NO: 568-S5-LHR-SEQ ID NO: 69-NH2)
```

Synthesis of Peptidomimetics.

Peptidomimetics were designed based on analogy to the native PIP1 peptide structure using Oncolexis software using a pool of 10000 virtual library, 61 virtual hits identified and were then optimized to give the best possible pharmacokinetic properties. All the 61 virtual hits were synthesized ay ChemDiv.

Example 2—Results

Identification of PELP1 Inhibiting Peptides.

To identify peptide that bind PELP1 with high affinity, the inventors performed a yeast-two-hybrid screen using a random peptide library from Clontech as prey and four domains of PELP1 (amino acids 1-400, 400-600, 600-866, and 960-1130) as the baits. This screen resulted in the identification of about 100 hits (FIG. 1A). Positive clones were sequenced and peptides were synthesized through GenScript with an additional TAT sequence for cell permeability. An initial screen was performed to test the effect of the peptides on PELP1-mediated breast cancer cell proliferation. Two of the peptides PIP1 (PELP1 Inhibiting Peptide 1) and PIP2 (PELP1 Inhibiting Peptide 2) were found to significantly inhibit PELP1-mediated proliferation. While the control TAT peptide had no significant effect, PIP1 was found to be more efficient at inhibiting proliferation than PIP2 (FIG. 1B). The inventors confirmed cellular uptake of the peptides by fluorescent microscopy with fluorescein tagged peptides. PIP1 was found to enter the cell membrane at 30 minutes and the nucleus by 120 minutes (FIG. 1C). They then validated peptide binding to PELP1 via a peptide pull-down assay using nuclear lysates from ZR75 cells (FIG. 1D). The peptides were tagged with biotin, bound to avidin beads and incubated in the nuclear lysates for one hour. PIP1 had a higher affinity to bind to PELP1 than PIP2 that is concordant with the differences seen in the cell proliferation assays (FIG. 1D). The PELP1-peptide binding was also confirmed using purified, full-length bacterial PELP1 (FIG. 7A).

PIPs Disrupt PELP1 Interactions with G9a/EHMT2 Complex.

Both PIP1 and PIP2 peptides had sequence homology to the histone lysine methyltransferase G9a/EHMT2/Bat8/KMT1C. Therefore, the inventors performed a co-immunoprecipitation in ZR75-PELP1 cells and found G9a to be in a complex with PELP1 (data not shown). In an in vitro competition assay, the PELP1 interaction with G9a/EHMT2 was disrupted by the addition of either of the two peptides in a dose-dependent manner while the control TAT peptide had no effect (FIG. 9).

PIP1 Inhibits PELP1 Co-Activation of ER Genomic Functions.

Figure 10:
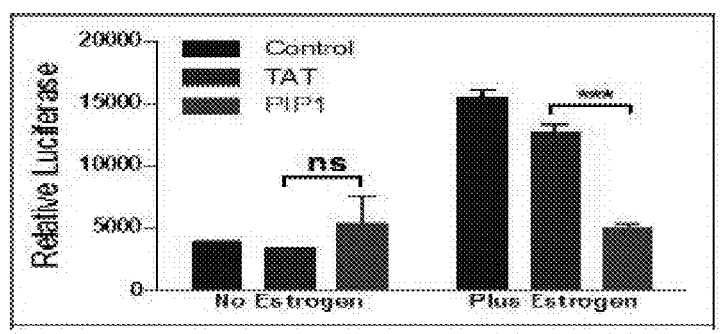
FIG. 10. ERE-luciferase assay. ZRPELP1 cells were transfected with ERE-luciferase and treated with either TAT or PIP1 for 24 hrs and with estradiol for 12 hrs.

The inventors next determined the effect of PIP treatment on PELP1's oncogenic functions. Since PELP1 is a co-activator of ERα, we performed a gene reporter assay using ERE-luciferase. As expected, PELP1 overexpressing cells had high ERE activation when treated with estradiol; however, the cells treated with PIP1 had significantly decreased ERE activation compared to the control TAT treated cells (FIG. 10).

PELP1 Interacts with G9a and PIPs Disrupt PELP1-G9a Complex.

Both PIP1 and PIP2 peptides have sequence homology to the histone lysine methyltransferase G9a/EHMT2/Bat8/KMT1C. This raised the possibility that PELP1 interacts with G9a. To test this possibility, the inventors performed a co-immunoprecipitation with nuclear lysate from ZR75-PELP1 cells treated with estradiol and found G9a to be in a complex with PELP1 (FIG. 2A). They failed to see PELP1 interaction with G9a in the absence of estradiol (data not shown). A GST binding assay showed that G9a binds to the 800-866 region of PELP1 which is also the region that the peptides were identified to bind to PELP1 in the yeast two hybrid screen (FIG. 2B). In a competition assay, the PELP1-G9a complex was disrupted by the addition of either of the two peptides in a dose-dependent manner while the control TAT peptide had no effect (FIGS. 2C, 7B). Since a recent study showed that G9a is a coactivator of ERα by binding through its N-terminal domain, the inventors determined whether PELP1, G9a and Eα form a complex that can be disrupted by PIP1 (Purcell et al., 2011). They observed that ERα enhances formation of the PELP1-G9a complex and treatment with PIP1 prevents the three proteins from forming a complex (FIG. 2C). To further characterize the PELP1-G9a complex, the inventors performed an ERE-luciferase reporter gene assay in ZR75 cells and found PELP1 and G9a to synergistically activate the estrogen response which is inhibited by PIP1 treatment (FIG. 2D).

PELP1 Affects G9a Activity and Modulates Activation of Unique Pathways.

Since G9a is a histone lysine methyltransferase, the inventors next determined whether PELP1 status affects G9a's methyltransferase activity. In an in vitro histone methyltransferase assay, the addition of purified PELP1 inhibits the ability of G9a to dimethylate Histone H3 Lysine 9 (FIG. 3A). To examine whether the effect PELP1 has on G9a translates in vivo at the transcriptional level, the inventors determined the effect of PELP1 knockdown or PIP1 treatment on the expression of G9a target genes Pecam1, Serac1, Rb1 and Bmi1. Both PIP1 treatment and PELP1 knockdown resulted in a decrease in the expression G9a upregulated target genes (FIG. 3B). Since PELP1 affects G9a's activity, the inventors analyzed PELP'1 global regulation of H3K9me2 through ChIP-sequencing analysis. H3K9me2 was immunoprecipitated from ZR75 and ZR75PELP1KD cells were treated with estradiol, a DNA library was prepared and ChIP-sequencing was performed. Location analysis of H3K9me2 peaks revealed a large percentage in enhancer regions in both control and knockdown cells (FIGS. 3C, 3E). Ingenuity pathway analysis of the genes at the binding peaks showed the pathways regulated by PELP1 through H3K9 dimethylation (FIGS. 3D, 3F). ChIP-sequencing results showed that PELP1 knockdown significantly affected the histone demethylation pattern in a number of genes. Pathway analysis of the top methylated genes in PELP1 knockdown cell revealed matrix metalloproteases (MMPs), axonal guidance and estrogen biosynthesis as the top pathways (FIG. 3F). Since PELP1 is shown to modulate the expression of several of these genes including several MMPs, increased histone dimethylation in the absence of PELP1 suggests that PELP1 mediates the expression of a subset of its target genes by modulating G9a functions.

Effect of PIPs on PELP1 Oncogenic Functions.

The inventors next determined the effect of PIP treatment on PELP1's oncogenic functions. PIP1 treatment at 10 μM causes a significant decrease in ZR75, ZR75PELP1, MCF7 and MCF7PELP1 cells, while deletion of any region of the peptide sequence decreases this effect (FIG. 4A). To confirm the effect of the peptides is through PELP1, they performed proliferation assays on ZR75PELP1KD and MCF7PEP1KD cells with increasing doses of PIP1 treatment and only saw an effect at very high concentrations (FIGS. 8A-B). Since PELP1 is a co-activator of ERα, the inventors tested the effect of PIPs on PELP1-mediated ERα coactivation using an ERE-luciferase reporter assay. As expected, PELP1 overexpressing cells had high ERE activation when treated with estradiol; however, the cells treated with PIP1 and PIP2 had significantly decreased ERE activation compared to the control TAT treated cells (FIG. 4B). To look at the effect of peptide treatment on estrogen-mediated growth, ZR75 cells were stimulated with estradiol and treated with TAT or PIP1, and PIP1 treatment resulted in an inhibition of the estrogen-mediated growth (FIG. 4C). The inventors then tested the effect of the peptides on the proliferation of therapy resistant cell lines MCF7-TamR and MCF7-LTLT. Both peptides inhibited the proliferation of MCF7-TamR and MCF7-LTLT cells and PIP1 treatment showed a synergistic inhibition of proliferation with tamoxifen (FIGS. 4D-E). To confirm specificity of PIP1 on ERα coactivation functions, the inventors tested the effect of PIP1 treatment on the Beta-catenin reporter, which is independent of ERα, and saw no significant effect on reporter activity (FIG. 7C). The inventors also analyzed the effect of peptide treatment on the proliferation of triple negative breast cancer cell lines MDA-MB-231 and MDA-MB-468 and saw no significant decrease in proliferation (FIG. 8C). Also, peptide treatment does not cause any change in ERα protein levels or have any associated toxicity (FIGS. 7D-E).

In Boyden-chamber assays using ZR75, ZR75PELP1, MCF7 and MCF7PELP1 cell. PIPs treatment significantly decreased the PELP1-mediated migratory ability of the PELP1 overexpressing cells (FIG. 5A). To test the effects of PIPs on PELP1-mediated anchorage independence, the inventors performed a soft agar assay with ZR75 and ZR75PELP1 cells treated with TAT, PIP1 or PIP2 (10 μM) every three days. ZRPELP1 cells treated with PIP1 had a substantial decrease in colony formation compared to controls (FIG. 5C). Further analysis of the PIP1-mediated growth inhibitory effect revealed that PIP1 treatment induces apoptosis of breast cancer cells as analyzed by TUNEL assay (FIG. 5D).

Effect of PIP1 on Mammosphere Formation.

Recent studies showed that G9a plays a critical role in the maintenance of genes in stem cells (Chen et al., 2012). Since knockdown of PELP1 was found to inhibit the stem cell maintenance G9a target gene Bmi1, the inventors went on to determine whether PELP1 has a role in cancer stem cells. In a FACS analysis of ZR75, ZR75PELP1 and ZR75PELP1KD cells, the percentage of $Cd44^{high}/CD22^{low}$ cells correlates with PELP1 status (FIG. 6A). Therefore, the inventors performed a mammosphere formation assay to determine whether PIP1 can inhibit the formation of mammospheres. MCF7PELP1 $Cd44^{high}/CD22^{low}$ cells were treated with TAT or PIP1 (10, 20 and 50 μM) when the cells were plated in serum free mammosphere media and treated again at five days. There was a significant decrease in the number of mammospheres that formed from the PIP1 treated cells and the size of the mammospheres was also substantially decreased (FIG. 6B). To further test the effect of PIP1 on self-renewal, the inventors dissociated the mammosphere, replated them to assay for self-renewal, and found the PIP1 treated cells to have decreased self-renewal capacity (FIG. 6C). Collectively, these results suggest that PIP1 has the potential to modulate the stemness of breast cancer stem cells.

PIPs have Potential to Inhibit Growth of Therapy Resistant Cells.

Figure 11:
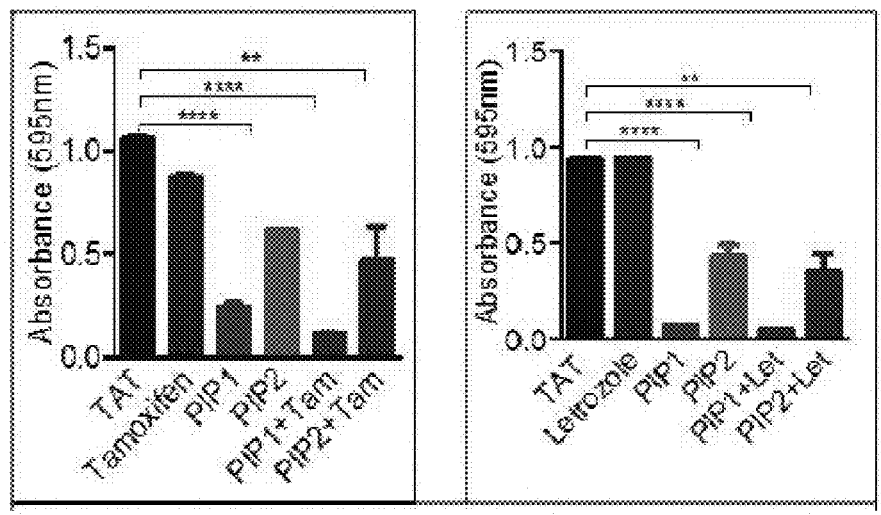
FIG. 11. Cell proliferation assay: letrozole-resistant MCF-7-LTLT cells and Tamoxifen resistant MCF7-Tam cells were treated with TAT, PIP1, or PIP2 (10 μM)+/− letrozole or Tamoxifen.

Since PELP1 deregulation is shown to contribute to therapy resistance, the inventors tested the effect of the peptides on the proliferation of therapy resistant cell lines MCF7-TamR and MCF7-LTLT. These model cells exhibit resistance to tamoxifen and letrozole therapy respectively. Both peptides inhibited the proliferation of MCF7-TamR and MCF7-LTLT (FIG. 11) cells and showed a synergistic inhibition of proliferation with hormonal therapy.

Figure 12:
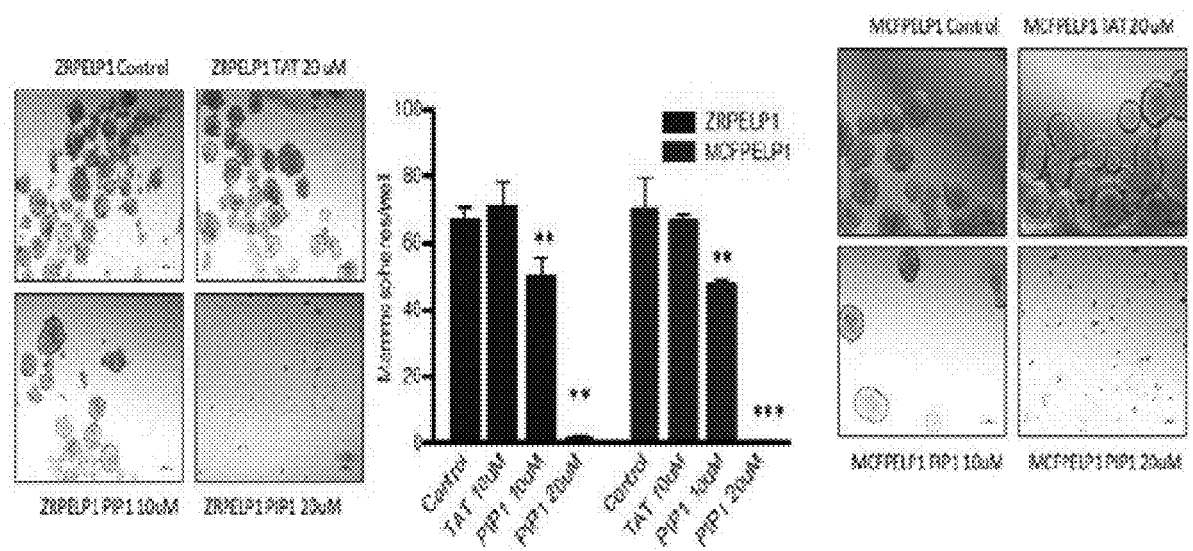
FIG. 12. Effect of PIP1 on mammosphere formation. Single-cell suspensions of ZR75-PELP1 were plated in triplicate wells at a density of 10,000 cells per ml in mammosphere medium in non-adherent plates. Cultures were treated with indicated concentration of PIP1 and mammospheres were counted after 7 days.

Effect of PIP1 on Proliferation of Cancer Stem Cells:

Evolving evidence suggests that cancer stem cells evade hormonal therapy and therapy resistance is thought to occur due to regrowth of tumor cells from cancer stem cells that escaped hormonal therapy or remain in the body after tumor resection. Therefore, the inventors performed a mammosphere formation assay to determine whether PIP1 can inhibit the formation of mammospheres (hall mark of stemness). ZRPELP1 and MCF7-PELP1 cells were treated with TAT or PIP1 (10 µM and 20 µM) when the cells were plated in mammosphere media and treated again at five days. There was a significant decrease in the number of mammospheres that formed from the PIP1 treated cells and the size of the mammospheres was also substantially decreased (FIG. 12).

Effects of PIP3 on Triple Negative Breast Cancer (TNBC) Proliferation.

Figure 13:
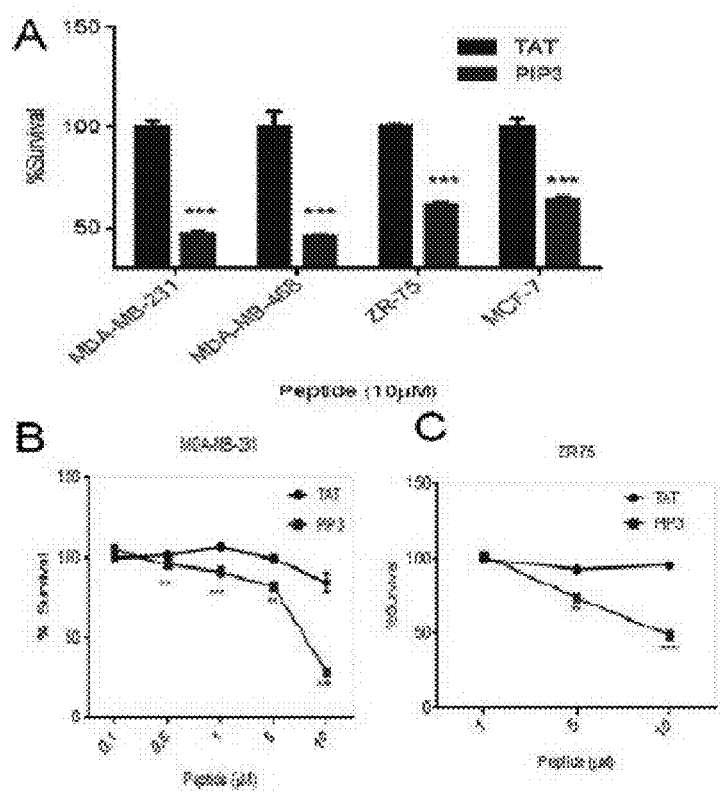
FIGS. 13A-C. PIP3 inhibits proliferation of breast cancer cells.

Recent studies showed PELP1 expression is also upregulated in triple negative breast cancer that do not express estrogen receptor and PELP1 is suggested to have ER independent oncogenic function in TNBC cells. The inventors tested whether PIPs have any activity on TNBC cells. These preliminary studies showed PIP3 but not PIP1 has activity in triple negative cells. As shown in FIGS. 13A-B, PIP3 treatment inhibited growth of both TNBC (MDA-MB-231 and MDA-MB-468) and ER-positive (ZR-75 and MCF-7) breast cancer cell lines.

Effect of PIP1 on Ovarian Cancer Cell Proliferation.

The inventors tested the effect of PIP1 treatment on ovarian cancer cells since PELP1 is also over expressed in ovarian cancer. PIP1 treatment significantly effected proliferation of the ovarian cancer model (BG1) cells. Treatment with PIP1 showed a dose-dependent decrease in the proliferation of the BG1 cells (FIG. 14). The inhibition of proliferation indicates the potential of the peptide in the treatment of ovarian cancers.

Effects of PIP1 and PIP3 on Glioma Proliferation.

Recent studies showed PELP1 expression is upregulated in high grade gliomas. Therefore, the inventors examined whether PIPs have any activity on glioma cells. As shown in FIGS. 15A-D, treatment of various glioma cell lines and primary GMB cells with either PIP1 or PIP3 significantly reduced their proliferation in a dose-dependent manner with PIP3 has more potent activity (5-10 µM) compared to PIP1 (50 µM).

Generation Stapled Peptide of PIP1 (sPIP1).

Stapled peptides are promising intracellular drug targets. Stapling of peptides increases cell penetrating ability and makes them resistant to proteases compared to non-stapled analogs. Stapling of peptides involves generation of hydrocarbon-stapled α-helical peptides locked into their bioactive α-helical fold through the site-specific introduction of a chemical brace, an all-hydrocarbon staple. To enhance translatability of PIPs, the inventors have designed stapled PIPs peptides (sPIPs) by incorporating special amino acids at i, i+4 position of the loop (FIGS. 16A-B). The inventors recently synthesized a small aliquot of stapled PIPs (sPIP3) and initial studies showed that staple modification enhanced delivery and therapeutic efficacy of the peptide (FIG. 16C).

Generation of Non-Peptide Peptidomimetics Based on PIP.

Bioactive peptides can be useful therapeutic agents. However, their degradation by peptidases and or poor bioavailability in vivo are problems to be selected as drug leads. To solve the problem, peptidomimetics have been proposed as substitutes for peptides in their interaction with receptors. In comparison with native peptides they show higher metabolic stability, better bioavailability, and longer duration of action. Peptidomimetics are designed based on analogy to the native peptide structure, then optimized to give the best possible pharmacokinetic properties.

Figure 17:
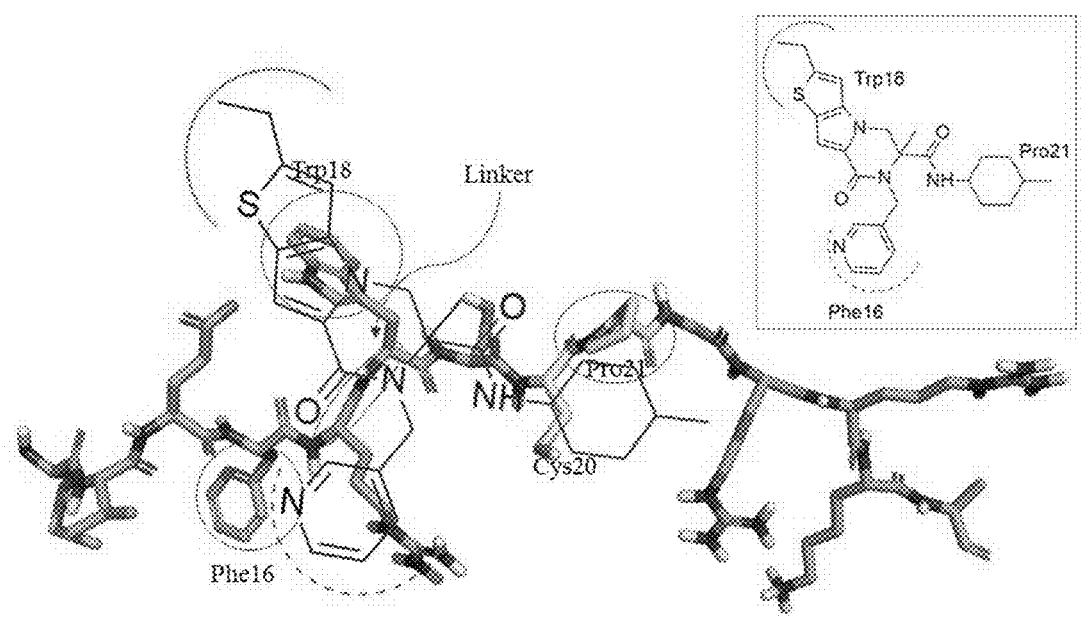
FIG. 17. Predicted Conformation of Peptide PIP1/Shape and Pseudo binding model of PELP1.
Figure 18:
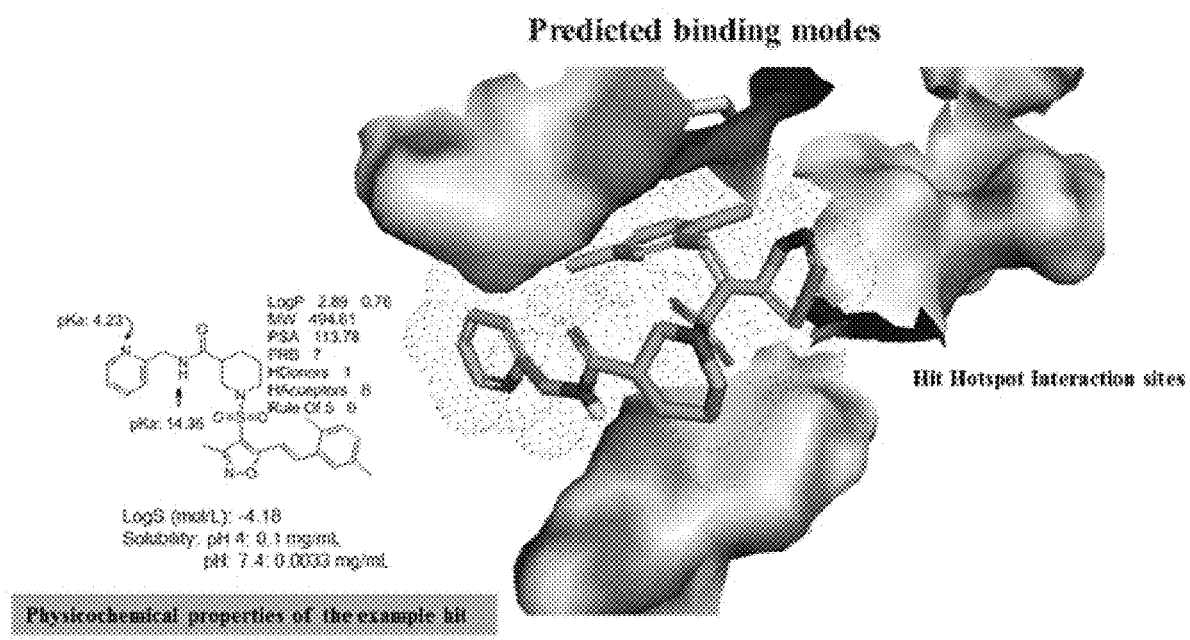
FIG. 18. Predicted Binding mode of Lead in Complex with Hypothetical Active site of PELP1. Sixty-one hits from 10,000 virtual compound library peptidomimetics.
Figure 19:
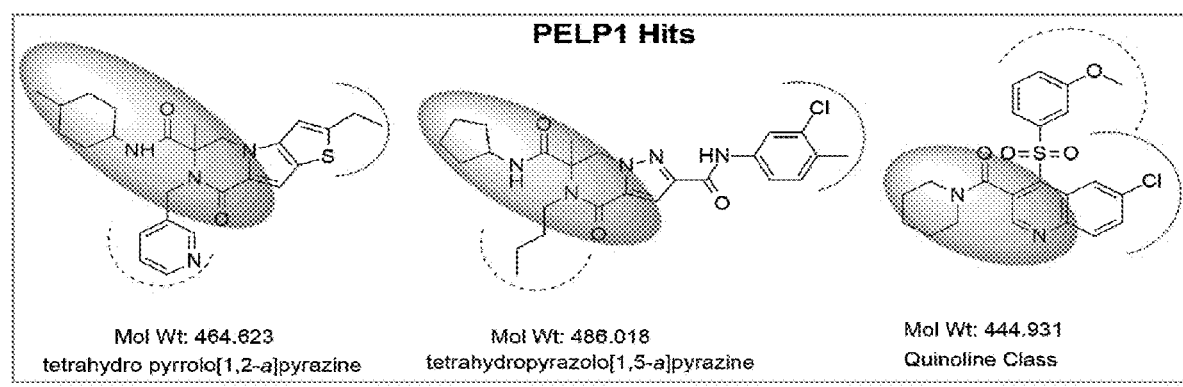
FIG. 19. Predicted Binding mode of three Lead Hits in Complex with Hypothetical Active site of PELP1.
Figure 20:
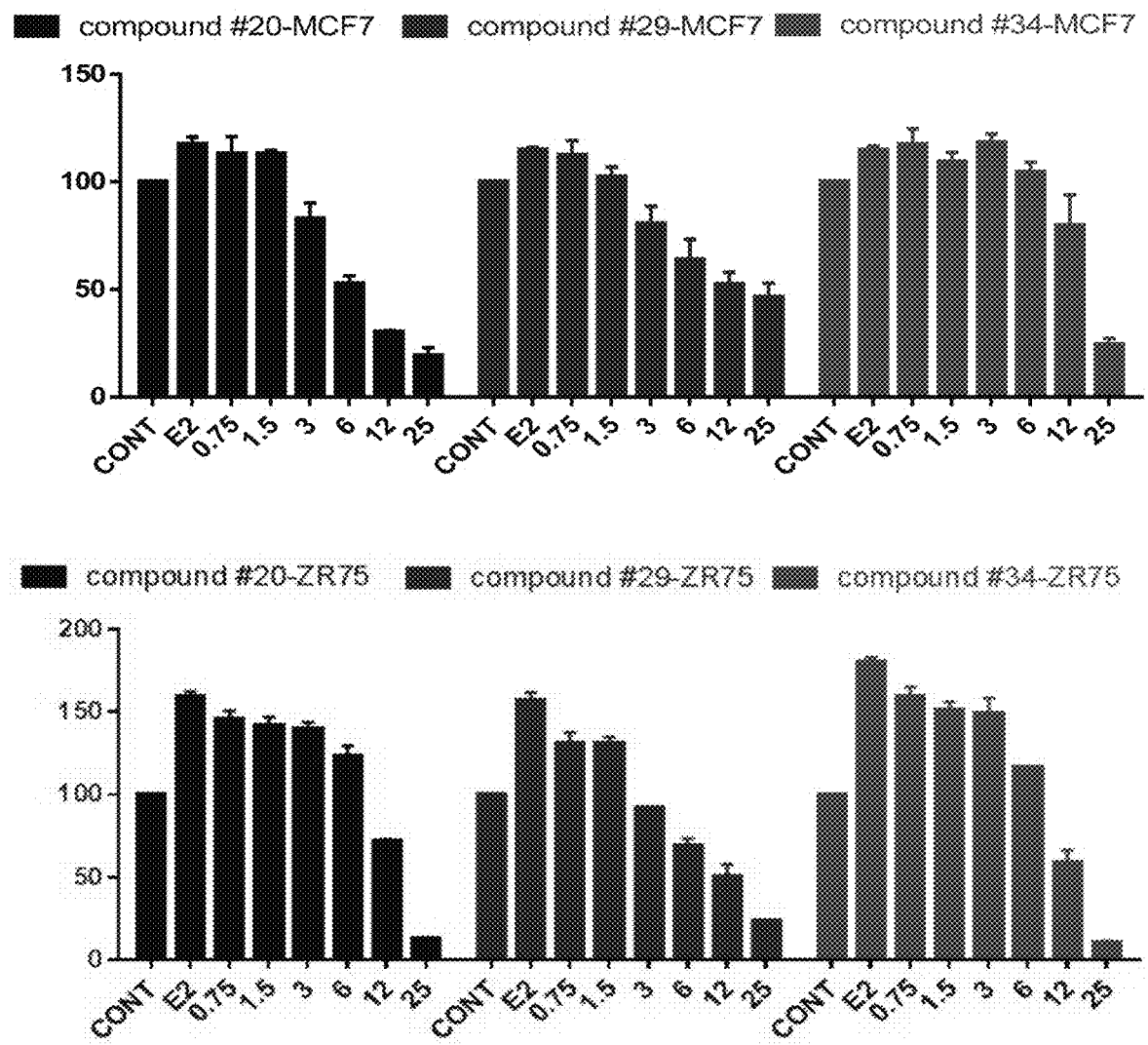
FIG. 20. Peptidomimetics (#20, 29, and 34) inhibit proliferation of breast cancer cells. MCF7 and ZR75 breast cancer cells were treated with vehicle or varying concentration of peptidomimetics and proliferation was measured by using the MTT assay.

The inventors used the Hit-Ligand interaction site with the PIP1 hot spot residues based on 3D alignment and shape (FIG. 17) and identified 61 potential hits from Ligand-Based screening using a 10,000 Diverse Set (FIG. 18). Screening of these 61 potential hits using MTT based cell viability assays identified three lead compounds (peptidomimetic #20, #29, #34) (FIG. 19). All there peptidomimitics (#20, #29, #34) showed expected activity similar to PIP1 in assays using two different breast cancer model cells (FIG. 20). Elucidation of Tanimoto Coefficient T=0.76 for both compound #20 and compound #34 confirmed that they had similar binding mode and on target specific for PELP1. With reference to compound #34, a quinoline class of compound is more cell permeable and thus may be more active in cells. Based on predicted/calculated physicochemical/ADME characteristics all three hits fall under drug like small molecules category.

Example 3—Discussion

In this study, the inventors have targeted oncogenic ERα-PELP1 signaling through disruption of PELP1's protein-protein interactions. They have screened a random peptide library to identify PELP1 binding peptides that interfere with PELP1-mediated oncogenic functions and developed them as novel cell permeable PELP1-Inhibiting Peptides 1 and 2 (PIP1, PIP2). They found that the peptides inhibit several of PELP1's oncogenic functions including ERα coactivation, proliferation, migration, anchorage independence, mammosphere growth and hormonal therapy resistance. Mechanistic studies showed that PELP1-mediated oncogenic functions involve G9a and PIPs interfere with PELP1-G9a interactions.

Since PELP1 expression is commonly deregulated in many hormonal cancers and because PELP1 is an independent prognostic marker of decreased breast cancer survival, drugs that block PELP1 function will have the potential to reduce breast cancer progression leading to therapy resistance and metastasis (Habashy et al., 2010). These studies identified PIPs as novel inhibitors of PELP1 oncogenic function. Successful testing of the PIPs in vivo will facilitate the development of individualized treatment driven by PELP1 status as a diagnostic marker. PIPs are advantageous over currently available chemotherapeutic drugs to treat advanced breast cancer due to their specificity, decreased side effects and are amenable to translation to clinical trials for treating patients with breast cancer. Recent studies have shown the feasibility of a stapled peptide approach to develop druggable peptide inhibitors, and Aileron Therapeutics recently started a Phase I clinical trial using a stapled-peptide drug (Walensky et al., 2004; Phillips et al., 2011; Grigoryev, 2013). These stapled peptides have a higher affinity for their target, enter cells more easily, are less readily degraded, and bind tightly to target proteins. Ongoing studies are focused on developing PIP stapled peptides to enhance their ability to translate to the clinic.

The peptide sequences led us to identify a novel PELP1 interacting protein, the histone lysine methyltransferase G9a, which is also a relevant target for cancer therapy. G9a has elevated expression in aggressive lung cancer cells which correlates with poor prognosis (Chen et al., 2010). Knockdown of G9a in prostate cancer cells results in decreased cell growth and morphological changes with loss of telomerase activity and shortened telomeres (Kondo et al., 2008). Also, there is higher expression of G9a in hepatocellular carcinoma in which H3K9me2 and DNA methylation coordinate to silence p16 (Kondo et al., 2007). G9a methylation of p53 at Lys 373 correlates with inactive p53 while reduction of G9a leads to a larger population of apoptotic cells (Huang et al., 2010). BIX-01294 inhibits G9a transiently and modulates H3K9me2, and BRD4770 induces senescence in PANC-1 cells only in cells with mutant p53 (Kubicek et al., 2007; Yuan et al., 2013). G9a knockdown in PC3 cancer cells inhibited cell growth and led to morphologically senescent cells with telomere abnormalities suggesting that G9a is required for hTERT expression and telomere maintenance (Kondo et al., 2008). Collectively, these studies suggest that G9a is a potential inhibitory target for cancer treatment along with PELP1 inhibition.

Currently, a major clinical problem is the development of resistance to hormonal therapy in breast cancer patients. While tamoxifen and other hormonal therapies target the estrogen receptor, changes in ERα coregulator expression such as PELP1 can also substantially contribute to ERα activity and correlate with a poor prognosis (List et al., 2001; Torres-Arzayus et al., 2004; Azorsa et al., 2001). ERα coregulator protein levels are tightly regulated under normal conditions with deregulation implicated in breast cancer progression. There is a critical need for alternate agents to target ERα coregulator oncogenic signaling. The results from this study suggest that the PELP1 inhibiting peptides PIP1 and PIP2 efficiently reduce the growth of therapy resistant cells and thus represent first generation inhibitors of PELP1 that can be further developed as drugs to treat patients with therapy resistance.

Another problem that patients face besides therapy resistance is disease recurrence that is thought to occur due to cancer stem cells that remain after tumor resection. Recent studies suggest that estrogen stimulates breast cancer stem-like cells, and G9a is shown to play a critical role in stem cell maintenance (Fillmore et al., 2010; Tachibana et al., 2002; Eptztejn-Litman et al., 2008). G9a knockout mice show prolonged expression of Oct3/4, a gene important for pluripotency, and delayed development (Yamamizu et al., 2012; Feldman et al., 2006). G9a acts as a master regulator that inactivates numerous early-embryonic genes by bringing about heterochromatinization of methylated histone H3K9 and de novo DNA methylation (Eptztejn-Litman et al., 2008). Here, the inventors have shown that PELP1 status correlates with cancer stem cell levels and treatment with PIP1 inhibits the self-renewal of the cancer stem cells. These results further implicate PELP1 as a critical breast cancer therapeutic.

In summary, these results show for the first time the identification and characterization of novel cell permeable peptide drugs (PIPs) that efficiently interfere with PELP1 oncogenic functions. Since PELP1 expression is commonly deregulated in breast cancer and is implicated in therapy resistance, PIPs will be useful in the treatment of advanced breast cancers. Future studies are needed to test the efficacy of PIPs using preclinical models and to convert PIPs into stable peptides to increase their efficacy in vivo.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCED

The following references, to the extent that they provide exemplary procedural or other details supplementary to those set forth herein, are specifically incorporated herein by reference:

U.S. Pat. No. 5,440,013
U.S. Pat. No. 5,446,128
U.S. Pat. No. 5,475,085
U.S. Pat. No. 5,597,457
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,790,421
U.S. Pat. No. 5,840,833
U.S. Pat. No. 5,859,184
U.S. Pat. No. 5,889,155
U.S. Pat. No. 5,929,237
U.S. Pat. No. 6,093,573
U.S. Pat. No. 6,261,569
U.S. Pat. No. 7,192,713
U.S. Pat. No. 7,183,059
U.S. Patent Publication 2005/02506890
U.S. Patent Publication 2005/0015232
U.S. Patent Publication 2006/0008848
Bodanszky et al., *J. Antibiot.*, 29(5):549-53, 1976.
Cohen et al., *J. Med. Chem.*, 33:883-894, 1990.
Fischer, *Med. Res. Rev.*, 27(6):755-796, 2007.
Gronenborn et al., *Anal. Chem.*, 62(1):2-15, 1990.
Jackson, *Seminars in Oncology*, 24:L164-172, 1997.
Johnson et al., *In: Biotechnology And Pharmacy*, Pezzuto et al. (Eds.), Chapman and Hall, NY, 1993.
Jones et al., *J. Med. Chem.*, 39:904-917, 1996.
McPherson, *J. Biol. Chem.*, 251:6300-6306, 1976.
Merrifield, *J. Am. Chem. Soc.*, 85:2149-2154, 1963.
Navia et al., *Curr. Opin. Struct. Biol.*, 2:202-210, 1992.
PCT Appln. PCT/US00/03745
PCT Appln. PCT/US00/14667
PCT Appln. PCT/US99/11913
PCT Appln. PCT/US99/18441
Peptide Synthesis, 1985
Protective Groups in Organic Chemistry, 1973
Protein NMR Spectroscopy, Principles and Practice, J. Cavanagh et al., Academic Press, San Diego, 1996.
Remington's Pharmaceutical Sciences, $15^{th}$ Ed., 1035-1038 and 1570-1580, 1990.
Schafmeister et al., *J. Am. Chem. Soc.*, 122(24): 5891-5892, 2000.
Solid Phase Peptide Synthelia, 1984.
Wider, *BioTechniques*, 29:1278-1294, 2000.
Walensky et al., *Science* 305:1466-1470, 2004.
Osborne, *Breast Cancer Research and Treatment*, 51:227-238, 1998.
Harvey et al., *J Clinical Oncol.*, 17:1474-1481, 1999.
Bekri et al., *Cytogenetics and Cell Genetics*, 79:125-131, 1997.
Habashy et al., *Breast Cancer Research and Treatment*, 120:603-612, 2010.
Rajhans et al., *Cancer Research*, 67:5505-5512, 2007.

Girard et al., *Molecular Cellular Endocrinology* 382(1):642-51, 2014.
Vadlamudi et al., *Journal Biological Chemistry*, 276:38272-38279, 2001.
Vadlamudi et al., *Nuclear Receptor Aignaling*, 5:e004, 2007.
Nair et al., *Cancer Research*, 70:7166-7175, 2010a.
Kumar et al., *Clinical Cancer Research*, 15:4123-4130, 2009.
Nair et al., *Breast Cancer research*, 13:R80, 2011.
Vallabhaneni et al. *Breast Cancer Research and Treatment*, 130:377-385, 2011.
Cortez et al., *Breast Cancer Research*, 14:R108, 2012.
Mann et al., *Cancers*, 3:1691-1707, 2011.
Nishioka et al., *Genes & Development*, 16:479-489, 2002.
Mann et al., *Carcinogenesis* 34(7):1468-75, 2013.
Tachibana et al., *Journal Biological Chemistry*, 276:25309-25317, 2001.
Milner et al., *The Biochemical Journal*, 290 (Pt 3):811-818, 1993.
Brown et al., *Mammalian Genome*, 12:916-924, 2001.
Collins et al., *Nature Structural & Molecular Biology*, 15:245-250, 2008.
Purcell et al., *Journal Biological Chemistry*, 286:41963-41971, 2011.
Kondo et al., *PloS One*, 3:e2037m 2008.
Chen et al., *Cancer Research*, 70:7830-7840, 2010.
Kubicek et al., *Molecular Cell*, 25:473-481, 2007.
Liu et al., *Journal Medicinal chemistry*, 52:7950-7953, 2009.
Nair et al., *EMBO Reports*, 11:438-444, 2010b.
Wysocka, J., *Methods*, 40:339-343, 2006.
Shaw et al., *Journal Mammary Gland Biology Neoplasia*, 17:111-117, 2012.
Nair et al., *Cancer Research*, 64:6416-6423, 2004.
Chen et al., *Genes & Development*, 26:2499-2511, 2012.
Walensky et al., *Science*, 305:1466-1470, 2004.
Phillips et al., *Journal American Chemical Society*, 133: 9696-9699, 2011.
Grigoryev, Y., *Nature Bedicine*, 19:120, 2013.
Kondo et al., *Hepatology Research*, 37:974-983, 2007.
Huang et al., *Journal Biological Chemistry*, 285:9636-9641, 2010.
Yuan et al., *Cell Death & Disease*, 4:e690, 2013.
List et al., *Breast Cancer Research and Treatment*, 68:21-28, 2001.
Torres-Arzayus et al., *Cancer Cell*, 6:263-274, 2004.
Azorsa et al., *Breast Cancer Research and Treatment*, 70:89-101, 2001.
Fillmore et al., *Proceedings National Academy Sciences USA*, 107:21737-21742, 2010.
Tachibana et al., *Genes & Development*, 16:1779-1791, 2002.
Epsztejn-Litman et al., *Nature Structural & Molecular Biology*, 15:1176-1183, 2008.
Yamamizu et al., *Cell Stem Cell*, 10:759-770, 2012.
Feldman et al., *Nature Cell Biology*, 8:188-194, 2006.

The invention claimed is:

1. A pharmaceutical composition comprising (a) a peptide or peptoid comprising a full-length sequence selected from SEQ ID NO: 1, 2, 3, 65, 66, 67, or 68 and is no more than 30 residues in length and (b) a pharmaceutically acceptable carrier, buffer or diluent.

2. The composition of claim 1, wherein said peptide or peptoid is fused to a cell penetrating peptide.

3. The composition of claim 1, wherein said peptide is a stapled peptide or comprises a bridge.

4. The composition of claim 3, wherein said bridge comprises a linker, chemically modified side chains, or hydrocarbon stapling.

5. The composition of claim 4, wherein the linker comprises a modification that stabilizes an alpha-helical structure of said peptide.

6. A method of inhibiting a cancer cell in a subject comprising administering to said subject a peptide or peptoid that binds to PELP1 and blocks one or more estrogen receptor co-activation functions of PELP1, wherein said peptide or peptoid comprises a full-length sequence selected from SEQ ID NO: 1, 2, 3, 65, 66, 67, or 68 and is no more than 30 residues in length.

7. The method of claim 6, wherein the cancer cell is a prostate, breast, glioma or ovarian cancer cell.

8. The method of claim 6, wherein said peptide or peptoid is fused to a cell penetrating peptide.

9. The method of claim 6, wherein administering comprises intravenous, intra-arterial, intra-tumoral, subcutaneous, topical or intraperitoneal administration.

10. The method of claim 6, wherein administering comprises local, regional, systemic, or continual administration.

11. The method of claim 6, wherein inhibiting comprises inducing growth arrest of said tumor cell, apoptosis of said tumor cell and/or necrosis of a tumor tissue comprising said tumor cell.

12. The method of claim 6, further comprising administering to said subject a second anti-cancer therapy.

13. The method of claim 6, wherein said subject is a human.

14. The method of claim 6, wherein said peptide or peptoid is administered at 0.1-500 mg/kg/d.

15. The method of claim 6, wherein said estrogen receptor co-activator function comprises PELP1 binding to histone lysine methyltransferase G9a.

* * * * *